(12) United States Patent
Kobayashi et al.

(10) Patent No.: US 9,823,460 B2
(45) Date of Patent: *Nov. 21, 2017

(54) BLADE INSPECTION APPARATUS AND BLADE INSPECTION METHOD

(71) Applicant: OLYMPUS CORPORATION, Shibuya-ku, Tokyo (JP)

(72) Inventors: Eiichi Kobayashi, Tama (JP); Yutaka Konomura, Tachikawa (JP); Fumio Hori, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 678 days.

This patent is subject to a terminal disclaimer.

(21) Appl. No.: 14/336,784

(22) Filed: Jul. 21, 2014

(65) Prior Publication Data

US 2015/0035969 A1    Feb. 5, 2015

(30) Foreign Application Priority Data

Jul. 30, 2013    (JP) ................. 2013-157927

(51) Int. Cl.
*G02B 23/24*    (2006.01)
*G01B 11/24*    (2006.01)
(Continued)

(52) U.S. Cl.
CPC ......... *G02B 23/2484* (2013.01); *F01D 17/02* (2013.01); *F01D 21/003* (2013.01);
(Continued)

(58) Field of Classification Search
CPC .................................................. G02B 23/2484
See application file for complete search history.

(56) References Cited

U.S. PATENT DOCUMENTS 5,575,754 A    11/1996    Konomura
7,518,632 B2    4/2009    Konomura
(Continued)

FOREIGN PATENT DOCUMENTS

DE    19513930 A1    9/1996
EP    2597273 A2    5/2013
(Continued)

OTHER PUBLICATIONS

Extended European Search Report dated Mar. 30, 2015 issued in counterpart European Application No. 14178321.7.
(Continued)

*Primary Examiner* — James Pontius
(74) *Attorney, Agent, or Firm* — Holtz, Holtz & Volek PC

(57) ABSTRACT

A blade inspection apparatus has a borescope and a PC. The borescope has a distance sensor for detecting an insertion length when an insertion section of the borescope is inserted through a hole provided in a casing in which a rotor of an engine is housed, an acceleration sensor for detecting an attitude of the insertion section, and distance sensors for detecting two distances from the insertion section to two stator vanes on a stator. The PC compares the attitude and two distances detected in the borescope with the attitude and two distances relating to an inspection image stored in a HDD. When a match occurs therebetween, the PC outputs match information.

15 Claims, 20 Drawing Sheets

(51) Int. Cl.
*G01N 21/954* (2006.01)
*H04N 7/18* (2006.01)
*F01D 17/02* (2006.01)
*F01D 21/00* (2006.01)
*F01D 25/28* (2006.01)

(52) U.S. Cl.
CPC ............ *F01D 25/285* (2013.01); *G01B 11/24* (2013.01); *G01N 21/954* (2013.01); *G02B 23/2423* (2013.01); *G02B 23/2476* (2013.01); *H04N 7/183* (2013.01)

(56) References Cited

U.S. PATENT DOCUMENTS

| | | |
|---|---|---|
| 8,314,834 B2 | 11/2012 | Konomura |
| 9,316,564 B2* | 4/2016 | Kobayashi ............ A61B 1/0005 |
| 2005/0199832 A1 | 9/2005 | Twerdochlib et al. |
| 2013/0135457 A1 | 5/2013 | Kell et al. |
| 2015/0036150 A1 | 2/2015 | Kobayashi et al. |
| 2015/0168263 A1* | 6/2015 | Mueller ................ F01D 21/003 348/82 |

FOREIGN PATENT DOCUMENTS

| | | |
|---|---|---|
| GB | 2493770 A | 2/2013 |
| JP | 2007163723 A | 6/2007 |
| JP | 2008220672 A | 9/2008 |
| JP | 2009168774 A | 7/2009 |
| JP | 2015028542 A | 2/2015 |
| WO | 2013045108 A1 | 4/2013 |

OTHER PUBLICATIONS

Japanese Office Action (and English translation thereof) dated Jun. 27, 2017 issued in counterpart Japanese Application No. 2013-157927.

* cited by examiner

| IMAGE ID | SCOPE ID | ANGLE OF ROTATION | FIRST DISTANCE | SECOND DISTANCE |
|---|---|---|---|---|
| 00001 | 00101 | ... | ... | ... |
| 00002 | 00102 | ... | ... | ... |
| ⋮ | ⋮ | ⋮ | ⋮ | ⋮ |

FIG. 24

| IMAGE ID | SCOPE ID | INSERTION LENGTH | ANGLE OF ROTATION |
|---|---|---|---|
| 00001 | 00101 | ... | ... |
| 00002 | 00102 | ... | ... |
| ⋮ | ⋮ | ⋮ | ⋮ |

81A

BLADE INSPECTION APPARATUS AND BLADE INSPECTION METHOD

CROSS REFERENCE TO RELATED APPLICATION

This application claims benefit of Japanese Application No. 2013-157927 filed in Japan on Jul. 30, 2013, the entire contents of which are incorporated herein by this reference.

BACKGROUND OF THE INVENTION

1. Field of the Invention

The present invention relates to a blade inspection apparatus and a blade inspection method for inspecting blades of an engine.

2. Description of the Related Art

Inspections of blades of jet engines or the like have been conventionally performed. An inspector performs a blade inspection, for example, by inserting an insertion section of a borescope, i.e., an endoscope, into an engine from an access port provided in the casing of the engine and by producing on a monitor a display of an endoscopic image of a blade in the engine.

An endoscopic apparatus has been proposed with which automation of the inspection process (labor saving) is performed so that the number of inspection process steps in inspection of blades of an engine is reduced, as disclosed in Japanese Patent Application Laid-Open Publication No. 2007-163723, and which is thus capable of reducing the complicatedness in an object inspection. Ordinarily, however, a blade inspection is performed with a borescope held by an inspector.

When a defective is found in a blade by inspection, a need may arise to produce an enlarged display of the defective portion and examine the defective portion in detail, depending on the size of the defect. Therefore, borescopes of various view angles are provided. An inspector first inspects a blade through a large area by using a borescope of a wide view angle and thereafter performs a detailed inspection by using a borescope of a narrow view angle and displaying an enlarged image of a defective portion on a monitor. An observation window through which light is received from the object is disposed in a distal end portion in the insertion section of the borescope.

SUMMARY OF THE INVENTION

According to one aspect of the present invention, there is provided a blade inspection apparatus for inspecting a plurality of blades periodically disposed on a periphery of a rotating shaft of a rotor of an engine and rotated on the rotating shaft, the apparatus including a first insertion length detection section that detects a first insertion length of a first insertion section of a first endoscope when the first insertion section is inserted through a hole provided in a casing in which the rotor is housed, a first attitude detection section provided in the first endoscope, the first attitude detection section detecting a first attitude of the first insertion section, a storage section that, when a still image of one of the blades picked up by a second endoscope having a second insertion section, a second insertion length detection section that detects a same insertion length as the first insertion length detected by the first insertion detection section, and a second attitude detection section that detects a same attitude as the first attitude detected by the first attitude detection section is obtained, stores a second insertion length of the second insertion section detected by the second insertion length detection section, and a second attitude of the second insertion section detected by the second attitude detection section, an insertion length comparison section that makes a comparison between the first insertion length detected by the first insertion length detection section and the second insertion length stored in the storage section, an attitude comparison section that makes a comparison between the first attitude detected by the first attitude detection section and the second attitude stored in the storage section in a state where an insertion axis of the second insertion section at a time of detection of the second attitude and an insertion axis of the first insertion section coincide with each other, a first match output section that outputs first match information indicating that there is a match between the first length and the second length based on a result of comparison made by the insertion length comparison section, and a second match output section that outputs second match information indicating that there is a match between the first attitude and the second attitude based on a result of comparison made by the attitude comparison section.

According to another aspect of the present invention, there is provided a blade inspection apparatus for inspecting a plurality of blades periodically disposed on a periphery of a rotating shaft of a rotor of an engine and rotated on the rotating shaft, the apparatus including an attitude detection section provided in an endoscope, the attitude detection section detecting an attitude of an insertion section, and a distance detection section provided in the endoscope, the distance detection section detecting two distances from the insertion section to two objects in two directions perpendicular to an axis of the insertion section and opposite to each other.

According to still another aspect of the present invention, there is provided a blade inspection method of inspecting a plurality of blades periodically disposed on a periphery of a rotating shaft of a rotor of an engine and rotated on the rotating shaft, the method including detecting a first insertion length of a first insertion section of a first endoscope by a first insertion length detection section when the first insertion section of the first endoscope is inserted from a hole provided in a casing in which the rotor is housed, detecting a first attitude of the first insertion section by a first attitude detection section provided in the first endoscope, making a comparison between the first insertion length detected by the first insertion length detection section and a second insertion length of a second insertion section of a second endoscope detected by a second insertion length detection section provided in the second endoscope and capable of detecting a same insertion length as the first insertion length detected by the first insertion length detection section at a time of acquisition of a still image of one of the blades picked up by the second endoscope, making a comparison between the first attitude detected by the first attitude detection section and a second attitude of the second insertion section detected by a second attitude detection section provided in the second endoscope and capable of detecting a same attitude as the first attitude detected by the first attitude detection section at the time of acquisition of a still image of the blade in a state where an insertion axis of the second insertion section at the time of acquisition of the still image by the second endoscope and an insertion axis of the first insertion section coincide with each other, outputting first match information indicating a match between the first insertion length and the second insertion length based on a result of comparison between the first insertion length and the second insertion length, and outputting second match information indicating a match between the first attitude and the second attitude based on a result of comparison between the first attitude and the second attitude.

BRIEF DESCRIPTION OF THE DRAWINGS

FIG. 17 is a diagram showing the data structure of a photographing information recording file according to the first embodiment;

FIG. 24 is a diagram showing the data structure of a photographing information recording file according to the second embodiment.

DETAILED DESCRIPTION OF THE PREFERRED EMBODIMENTS

Embodiments of the present invention will be described below with reference to the drawings.

First Embodiment (Entire Construction)

Figure 1:
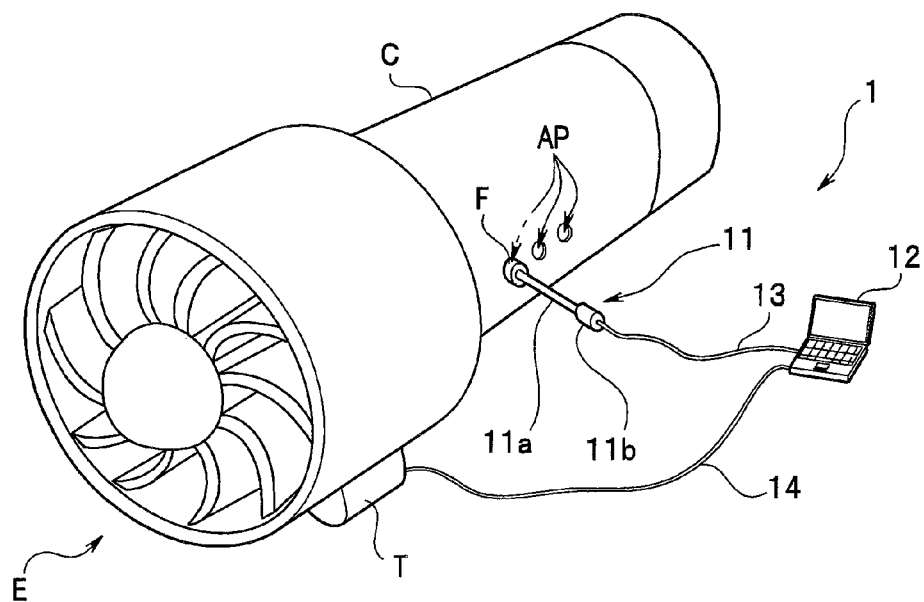
FIG. 1 is a perspective view for explaining a state of inspection of an engine according to a first embodiment of the present invention.
Figure 13:
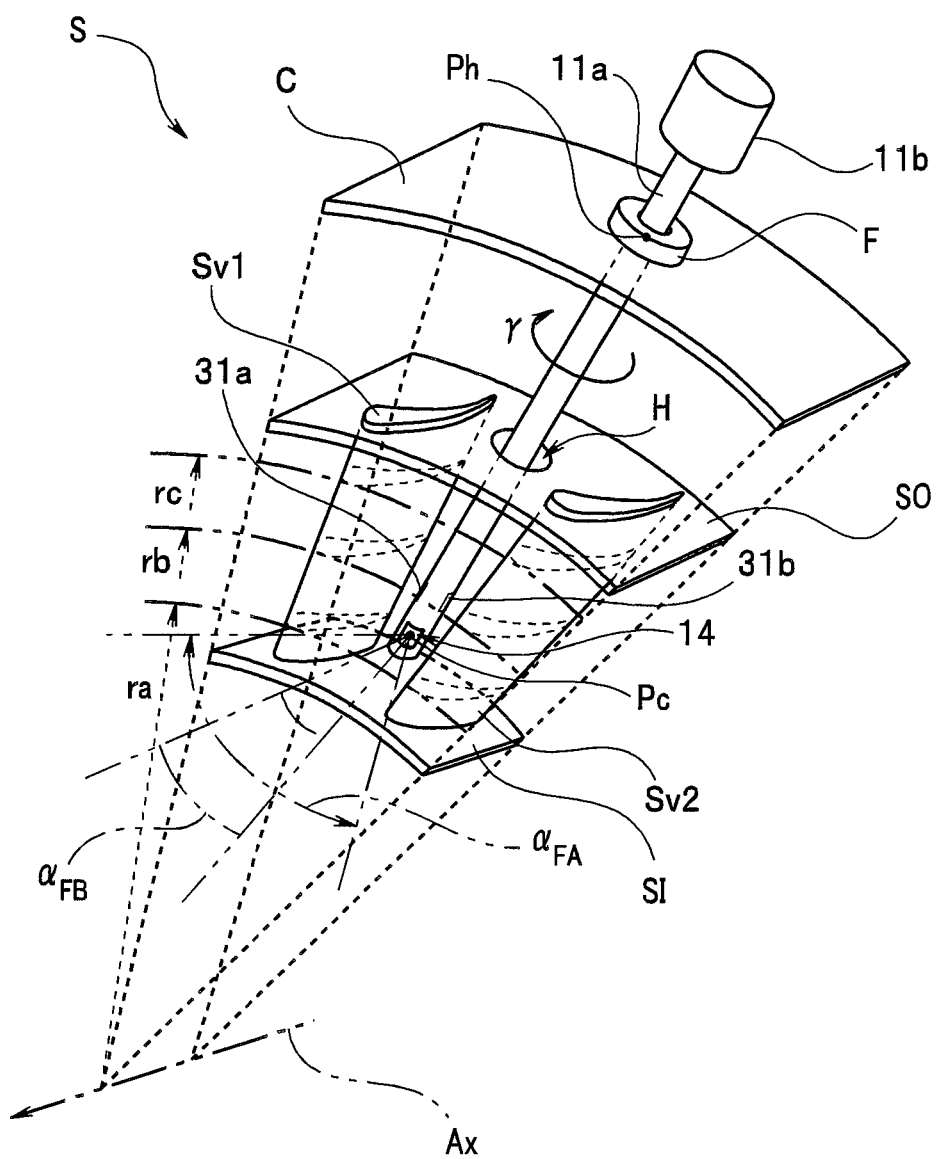
FIG. 13 is a perspective view of a portion of a stator S for explaining a state where an insertion section 11a is inserted in a casing C of an engine E according to the first embodiment.

FIG. 1 is a perspective view for explaining a state of inspection of an engine according to the present embodiment. In the present embodiment, an engine E is a jet engine. Description will be made of a case where a plurality of compressor blades (hereinafter referred to simply as "blades") in a compressor portion provided at the rear of an air intake portion are inspected with a blade inspection system. A turning tool T is connected to the engine E to enable a rotor R (FIG. 14) on which the plurality of blades are fixed to be rotated on an axis of rotation Ax (FIG. 13).

Note that while an example of inspection of the compressor blades is described below, inspection of other blades such as turbine blades can also be performed with the blade inspection system 1 in the present embodiment in the same manner.

The blade inspection system 1 includes a borescope 11 and a personal computer (hereinafter referred to as "PC") 12. The borescope 11 and the PC 12 are connected to each other through a signal cable (hereinafter referred to as "cable") 13. The borescope 11 has an insertion section 11a to be inserted into the engine E having a plurality of blades B to be inspected, and a grasping section 11b provided on a proximal end portion of the insertion section 11a.

The turning tool T and the PC 12 are connected to each other by a cable 14. The turning tool T is controlled according to an instruction from the PC 12 so as to rotate the rotor.

A casing C of the engine E has a plurality of (three in this example) access ports AP at predetermined positions. The insertion section 11a of the borescope 11 is an elongated rigid endoscope having such a diameter and length as to be capable of being inserted into the casing C through holes of any of the access ports AP to enable observation of the plurality of blades B disposed periodically about the axis of rotation Ax of the rotor R of the engine E.

When the insertion section 11a of the borescope 11 is inserted into the casing C, a fixing implement F is attached to the access port AP through which the insertion section 11a is to be inserted. The fixing implement F is an article of equipment for supporting and fixing the insertion section 11a of the borescope 11 at the position of the access port AP of the casing C. That is, the fixing implement F is constructed so as to be capable of being attached to the access port AP, to have an insertion hole Fa through which the insertion section 11a is passed and to be capable of supporting the borescope 11.

Figure 2:
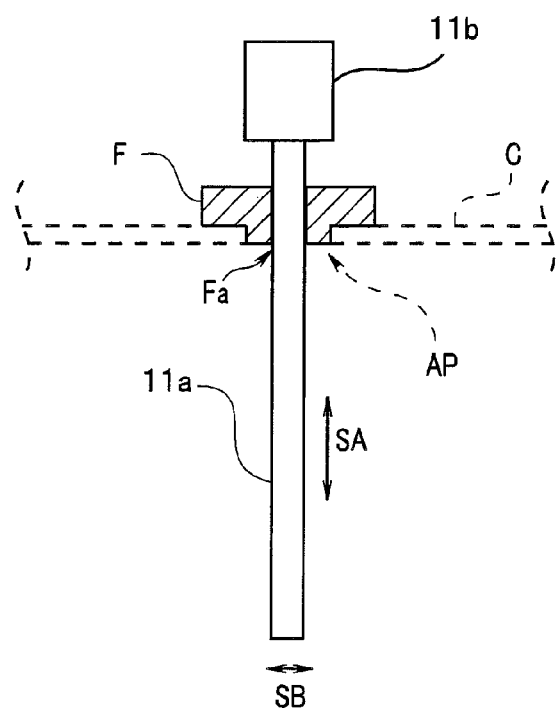
FIG. 2 is a diagram for explaining a state where a borescope 11 according to the first embodiment is fixed by a fixing implement F.

FIG. 2 is a diagram for explaining a state where the borescope 11 is fixed by the fixing implement F. The fixing implement F has a portion fitting to an opening shape of each access port AP provided in the casing C of the engine E and has such a configuration that the fixing implement F can be fixed on the access port AP.

An insertion hole Fa is formed in the fixing implement F. An inner peripheral surface of the insertion hole Fa has a shape conforming to the shape of an outer peripheral surface of the cylindrical insertion section 11a. That is, the insertion hole Fa is cylindrical. The insertion section 11a can therefore be moved in directions along the axis of the insertion section 11a indicated by arrows SA while being inserted through the insertion hole Fa.

While the insertion section 11a can be moved in directions along the axis of the insertion section 11a, the shape of the insertion section 11a is formed so that a distal end portion of the insertion section 11a is not moved in any of directions perpendicular to the axis of the insertion section 11a indicated by arrows SB.

Accordingly, a user as an inspector who inspects blades can insert the insertion section 11a into the insertion hole Fa of the fixing implement F, insert the insertion section 11a into the engine E while holding the borescope 11 with his/her hand, move the insertion section 11a to and fro along the insertion direction in the engine E, and freely rotate the borescope 11 about the axis of the insertion section 11a.

As described above, the blade inspection system 1 is a blade inspection apparatus for inspecting the plurality of blades B periodically disposed about the axis of rotation Ax of the rotor R of the engine E and rotating about the axis of rotation Ax.

(Construction of the Borescope)

Figure 3:
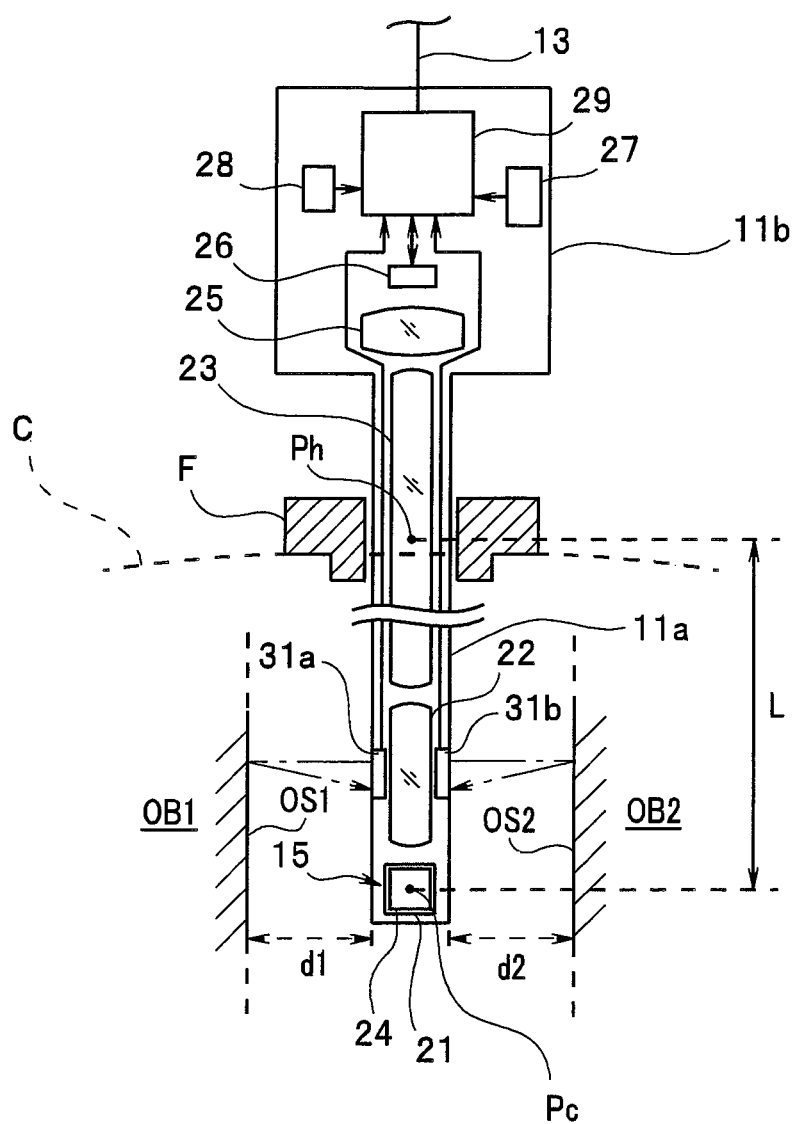
FIG. 3 is a diagram for explaining the construction of a borescope 11 according to the first embodiment.

FIG. 3 is a diagram for explaining the construction of the borescope 11.

An optical system for leading reflected light from an object to an image pickup device is disposed in the insertion section 11a. This optical system has a mirror 21, an objective optical system 22 and a relay optical system 23 disposed in the insertion section 11a. The mirror 21 is an optical component disposed in the distal end portion of the insertion section 11a. The mirror 21 directs toward the grasping section 11b light having entered through a glass plate 24 provided in an observation window 15 provided in a side surface of the distal end portion of the insertion section 11a. The objective optical system 22 is disposed in the insertion section 11a on the distal end side. The objective optical system 22 is an optical component for forming a real image of an object. The relay optical system 23 is an optical component for transmitting an image formed by the objective optical system 22 to the grasping section 11b.

Thus, the borescope 11 is a side-view type of endoscope provided with the observation window 15 in the distal end portion of the cylindrical insertion section 11a and the transparent glass member 24 in the observation window 15, and constructed so that light having been incident on the observation window 15 is incident on the mirror 21.

Note that an illumination device not illustrated is provided in the borescope 11. An object in such a position as to be opposed to the observation window 15 is illuminated with the illumination device. For example, the illumination device is constituted by a light source provided in the grasping section 11b and a light guide inserted in the insertion section 11a. The illumination device is provided so that light from the light source is emitted from the distal end portion of the insertion section 11a toward an object.

Two distance sensors 31a and 31b are disposed in the vicinity of the observation window 15 in the distal end portion of the insertion section 11a at a predetermined distance from the observation window 15. The direction along which reflected light from an object is incident on the mirror 21 is perpendicular to a line connecting centers of the two distance sensors 31a and 31b.

In the grasping section 11b, an image pickup optical system 25, a CCD 26, which is an image pickup device, an acceleration sensor 27, an ID storage unit 28 and a communication control unit 29 are provided.

The image pickup optical system 25 is an optical system that forms on an image pickup surface of the CCD 26 an object image emitted from the relay optical system 23. The CCD 26, which is an area sensor, is a solid-state image pickup device that makes photoelectric conversion of an object image formed by the image pickup optical system 25.

Note that while the CCD 26 is provided in the grasping section 11b and disposed so as to receive light having passed through the optical system in the insertion section 11a in the present embodiment, the CCD 26 may alternatively be provided in the distal end portion of the insertion section 11a.

The acceleration sensor 27 is a three-axis acceleration sensor. The communication control unit 29 calculates an angle of rotation γ of the borescope 11 about the axis from outputs from the acceleration sensor 27, as described below.

The ID storage unit 28 is a storage unit that stores a scope ID as information for identification of the borescope 11.

The communication control unit 29 includes a central processing unit (CPU) and a communication interface unit. The configuration of the communication control unit 29 is described later.

The distance sensors 31a and 31b are sensors that sense the distances to a surface of objects existing at such positions as to be opposed to the sensors. The distance sensors 31a and 31b are, for example, each a PSD distance sensor having a light source element that projects a spot of light and a position sensitive detector (PSD) element that detects the position of the centroid of a received spot of light. The PSD distance sensor detects the distance to the object by using the principle of triangulation.

In the present embodiment, the distance sensors 31a and 31b are detection units that are disposed at positions on the surface of the insertion section 11a symmetric about the axis of the insertion section 11a, and that respectively detect the distances to objects existing opposite from each other along a direction perpendicular to the axis of the insertion section 11a.

Accordingly, when as shown in FIG. 3 the insertion section 11a is positioned between two objects OB1 and OB2 so that the two distance sensors 31a and 31b can detect distances d1 and d2 to the two objects OB1 and OB2, the distance sensor 31a detects the distance d1 from the surface of the insertion section 11a to a surface OS1 of the first object OB1, and the distance sensor 31b detects the distance d2 from the surface of the insertion section 11a to a surface OS2 of the second object OB2. Each of the two distance sensors 31a and 31b measures the distance, for example, in a range of about 10 to 50 mm. That is, the distance sensors 31a and 31b are provided in the borescope 11, which is an endoscope, and constitute distance detection units that detect the two distances from the insertion section 11a to two objects (stator vanes Sv provided on a stator S of the engine E in this example) along two directions opposite to each other and perpendicular to the axis of the insertion section 11a.

In the present embodiment, the insertion section 11a is inserted between two stator vanes Sv of a stator S (FIG. 13). Accordingly, the surface OS1 of the first object OB1 is a surface of one stator vane Sv1 and the surface OS2 of the second object OB2 is a surface of the stator vane Sv2 adjacent to the first object OS1.

As described above, the two distance sensors 31a and 31b are provided on the side surface of the distal end portion of the insertion section 11a. The direction toward the object OB1 detected with the distance sensor 31a is perpendicular to the axis of the insertion section 11a and is opposite to the direction toward the object OB2 detected with the distance sensor 31b. The distance sensor 31a detects the distance d1 to the surface OS1, and the distance sensor 31b detects the distance d2 to the surface OS2.

Detection signals from the two distance sensors 31a and 31b and an image signal from the CCD 26 and respective detection signals from the acceleration sensor 27 and a scope ID signal from the ID storage unit 28 are inputted to the communication control unit 29.

Figure 4:
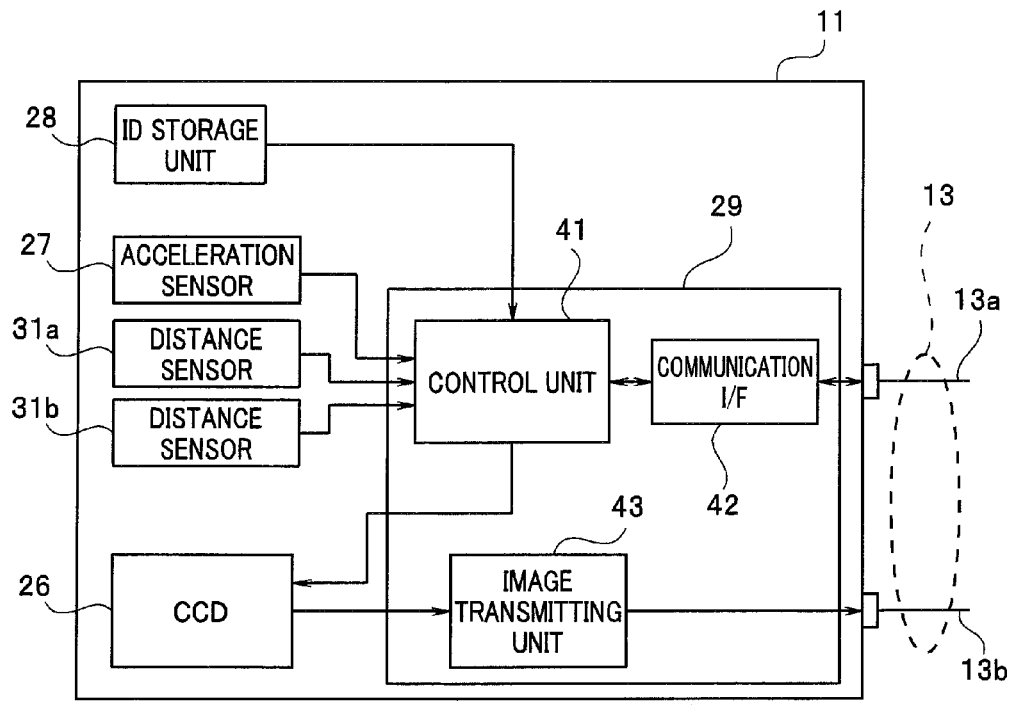
FIG. 4 is a block diagram showing the circuit configuration of the borescope 11 according to the first embodiment.

FIG. 4 is a block diagram showing the circuit configuration of the borescope 11. The communication control unit 29 includes a control unit 41, a communication interface unit (hereinafter referred to as "communication I/F") 42 connected to a signal line 13a in the cable 13 for the purpose of communicating with the PC 12, and an image transmitting unit 43 connected to a signal line 13b for transmitting the image signal from the CCD 26 to the PC 12. The communication I/F 42 is connected to the control unit 41 and to the signal line 13a in the cable 13 connected to the PC 12.

The control unit 41 includes a central processing unit (CPU), a ROM and a RAM, is supplied with output signals from the various sensors, executes a predetermined calculation process and outputs predetermined sorts of information to the PC 12 through the communication I/F 42.

The CCD 26, the acceleration sensor 27, the ID storage unit 28 and the distance sensors 31a and 31b are connected to the control unit 41.

The control unit 41 is supplied with the scope ID for the borescope 11 from the ID storage unit 28 and is also supplied with detection signals from the acceleration sensor 27 and the distance sensors 31a and 31b.

The control unit 41 supplies a drive signal to the CCD 26 to drive the CCD 26.

Note that in the following description, the insertion length L of the insertion section 11a is the distance from a point Ph at a center of the insertion hole of the fixing implement F to an image pickup optical center Pc in pickup of an image of an object through the observation window 15, as shown in FIG. 3.

From the shape of the fixing implement F, the center point Ph in the fixing implement F is determined in advance. The positional relationship with the image pickup optical center Pc in the insertion section 11a is also determined in advance.

Note that the insertion length L may be determined with reference to points other than the center point Ph and the image pickup optical center Pc.

The control unit 41 also calculates, as attitude information about the borescope 11, based on detection signals from the acceleration sensor 27, the angle of rotation γ of the borescope 11 about the axis.

The acceleration sensor 27 outputs three detection signals with respect to the direction of gravity g. Normalization processing is performed on the three outputted detection signals, and the angle of rotation γ is calculated based on the three detection signals thereby normalized. If three values Dx, Dy, and Dz are obtained by normalizing the three detection signals from the acceleration sensor 27, the angle of rotation γ is $\tan^{-1}(-Dy/Dx)$. Accordingly, the acceleration sensor 27 is provided in the borescope 11 to constitute an attitude detection unit that detects the attitude of the insertion section 11a. The attitude is defined with the angle of rotation γ about the axis of the insertion section 11a.

The control unit 41 calculates the distances d1 and d2 as two distance information items based on the values of the detection signals from the two distance sensors 31a and 31b, respectively.

The control unit 41 outputs, to the PC 12, in real time, through the communication I/F 42, the insertion length L and attitude information calculated based on the detection signals from the respective sensors.

The image signal outputted from the CCD 26 is converted into a digital signal in the image transmitting unit 43 and is outputted from the signal line 13b in the cable 13. The image transmitting unit 43 outputs the digital image signal in a differential signal format such as LVDS to the signal line 13.

(Configuration of PC)

Figure 5:
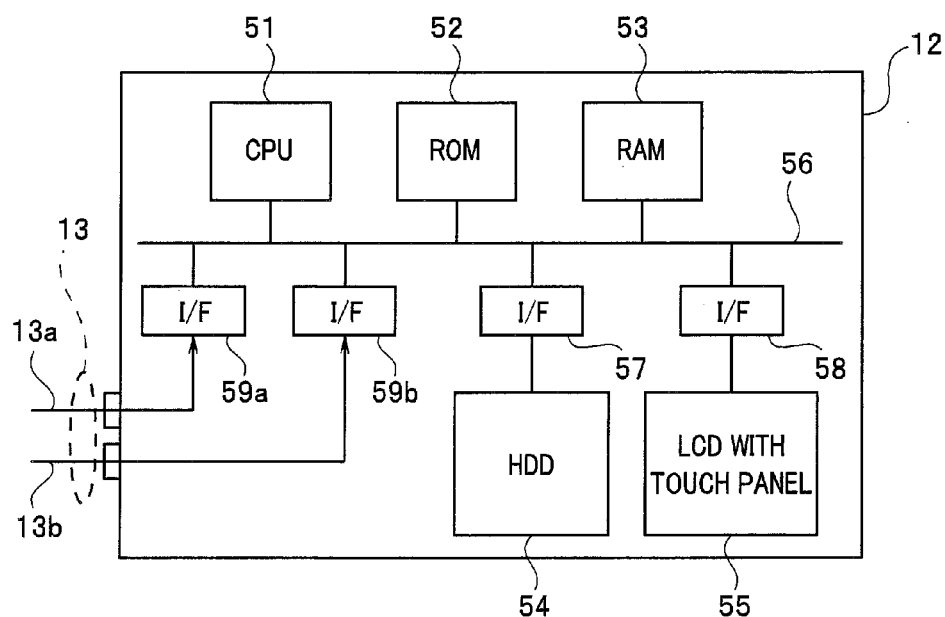
FIG. 5 is a block diagram showing the configuration of a PC 12 according to the first embodiment.

FIG. 5 is a block diagram showing the configuration of the PC 12. The PC 12 includes a central processing unit (hereinafter referred to as "CPU") 51, a ROM 52, a RAM 53, a hard disk drive (hereinafter referred to as "HDD") 54 and a liquid crystal display (hereinafter referred to as "LCD") 55. The CPU 51, the ROM 52 and the RAM 53 are connected to each other by a bus 56. The HDD 54 and the LCD 55 are connected to the bus 56 through interfaces (hereinafter referred to as "I/F") 57 and 58, respectively.

The LCD 55 is a display with a touch panel. The CPU 51 can cause the LCD 55 to display an endoscopic image, a predetermined menu view, a GUI view described below, and the like and can detect a command input from a user by receiving an output signal from the touch panel.

The PC 12 further has I/Fs 59a and 59b to which the signal lines 13a and 13b in the cable 13 are respectively connected. The PC 12 communicates with the control unit 41 through the I/F 59a, and receives image signals from the borescope 11 through the I/F 59b. A user can display as inspection image an image signal from the borescope 11 on the screen of the LCD 55 and can record the image signal in the HDD 54.

When an inspection image is recorded, the predetermined sorts of information obtained from the detection signals from the respective sensors or calculated with respect to the inspection image to be recorded are recorded together with the inspection image in the HDD 54. Accordingly, the HDD 54 constitutes a storage unit that stores the attitude of the insertion section 11a detected with the acceleration sensor 27 when a still image of a blade B picked up with the borescope 11 and the two distances from the insertion section 11a detected with the two distance sensors 31a and 31b at the time of this image pickup. In the present embodiment, information including the angle of rotation γ is recorded in image data on the inspection image as EXIF information for the image data, and the image data is stored in the HDD 54.

When the borescope 11 is connected to the PC 12 through the cable 13, the control unit 41 in the borescope 11 transmits the scope ID stored in the ID storage unit 28 to the PC 12 and to the CPU 51. The PC 12 can thus obtain the scope ID for the borescope 11.

The PC 12 can then obtain information on the attitude and the distances in real time from the borescope 11 through the communication I/F 59.

(Procedure of Inspection)

A user as an inspector who inspects blades first performs an overall inspection of the blades by using a borescope of a wide view angle. The user thereafter performs a detailed inspection by using a borescope of a narrow view angle and by displaying an enlarged image of a defective portion found in the preceding inspection.

Figure 6:
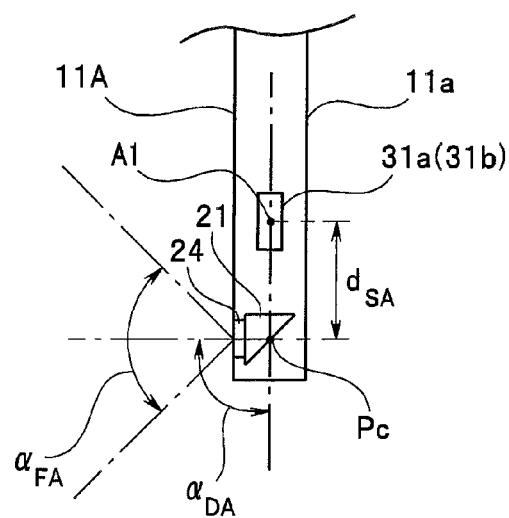
FIG. 6 is a diagram for explaining the view angle of a borescope 11A, which is comparatively wide, according to the first embodiment.
Figure 7:
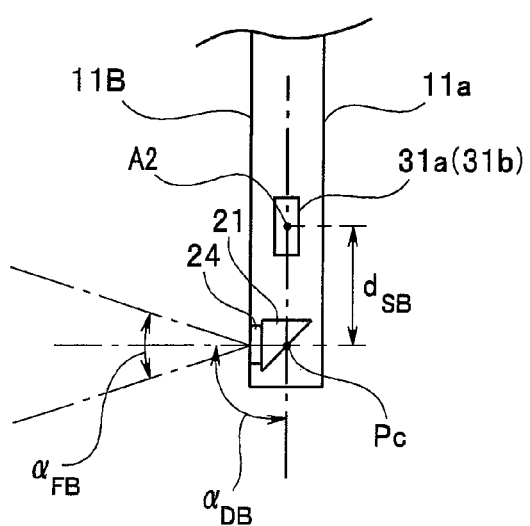
FIG. 7 is a diagram for explaining the view angle of a borescope 11B, which is narrower than that of the borescope 11A shown in FIG. 6, according to the first embodiment.
Figure 8:
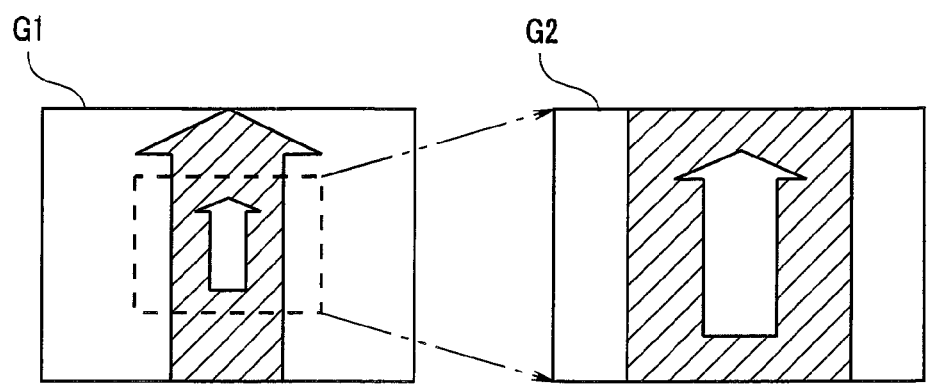
FIG. 8 is a schematic explanatory diagram for explaining the difference between endoscopic images picked up with the two borescopes differing in view angle according to the first embodiment.

FIGS. 6 and 7 are diagrams for explaining the difference in view angle between borescopes. FIG. 6 is a diagram for explaining the view angle of a borescope 11A, which is a comparatively wide. FIG. 7 is a diagram for explaining the view angle of a borescope 11B, which is narrower than that of the borescope 11A shown in FIG. 6. FIG. 8 is a schematic explanatory diagram for explaining the difference between endoscopic images picked up with the two borescopes differing in view angle.

Common details and the difference between the borescopes 11A and 11B will be described. The borescopes 11A and 11B are identical in external shape and size to each other. Also, as shown in FIGS. 6 and 7, distances $d_{SA}$ and $d_{SB}$ from the image pickup optical centers Pc passing through the optical axis centers of the mirrors 21 to axes A1 and A2 passing through two central positions in the two distance sensors 31a and 31b in the optical systems, as seen in side views of the borescopes 11A and 11B along the axes A1 and A2 passing through the two central positions in the two distance sensors 31a and 31b, are equal to each other. That is, the distance $d_{SA}$ from the image pickup optical center Pc of the mirror 21 to the axis A1 passing through the central positions in the two distance sensors 31a and 31b in the optical system of the borescope 11A is equal to the distance $d_{SB}$ from the image pickup optical center Pc to the axis A2 passing through the center positions in the distance sensors 31a and 31b in the borescope 11B.

The view angle $\alpha_{FA}$ of the borescope 11A shown in FIG. 6 is determined by the objective optical system 22, the relay optical system 23 and the image pickup optical system 25 in the borescope 11A. Similarly, the view angle $\alpha_{FB}$ of the borescope 11B shown in FIG. 7 is determined by the objective optical system 22, the relay optical system 23 and the image pickup optical system 25 in the borescope 11B. The view angle $\alpha_{FA}$ is larger than the view angle $\alpha_{FB}$.

Further, as shown in FIGS. 6 and 7, a viewing direction angle $\alpha_{DA}$ from the axial direction of the insertion section 11a of the borescope 11A is equal to a viewing direction angle $\alpha_{DB}$ from the axial direction of the insertion section 11a of the borescope 11B. Note that each of the viewing direction angle $\alpha_{DA}$ and the viewing direction angle $\alpha_{DB}$ in the present embodiment is 90 degrees.

That is, the borescope 11A has the insertion section 11a, the acceleration sensor that detects the same attitude as that detected by the acceleration sensor 27 of the borescope 11B, and the two distance sensors 31a and 31b that detect the same two distances d1 and d2 as the borescope 11B.

As described above, the respective parameters of the two borescopes 11A and 11B other than the view angles in the image pickup optical systems are equal to each other. Therefore, the image pickup optical centers Pc the two borescopes 11A and 11B in image pickup from an object coincide with each other when the borescopes 11A and 11B have the same insertion amount L and the same viewing direction.

Referring to FIG. 8, an inspection image G1 is an image picked up with the borescope 11A, and an inspection image G2 is an image picked up with the borescope 11B. Since the view angle $\alpha_{FB}$ of the borescope 11B is smaller than the view angle $\alpha_{FA}$ of the borescope 11A, the inspection image G2 is an enlarged image corresponding to a central portion of the inspection image G1. In the endoscopic image G2 shown in FIG. 8, a blank arrow in the inspection image G1 is enlarged.

If the insertion lengths of the insertion section 11a of the borescope 11A and the insertion section 11a of the borescope 11B are equal to each other, and if the directions from the image pickup optical centers Ps toward the object coincide with each other, the central-portion images in the inspection images G1 and G2 are images picked up from the same position on the blade B, as shown in FIG. 8.

The blade inspection system 1 assists the user in operating the borescope 11B so that after the user as an inspector has first observed and inspected the blade B with the borescope 11A, the user can observe and inspect, by using the borescope 11B having a narrower view angle, and by enlarging the image of the blade B, a defective portion found by inspection with the borescope 11A.

(Function)

The operation of the blade inspection system 1 will be described.

Figure 9:
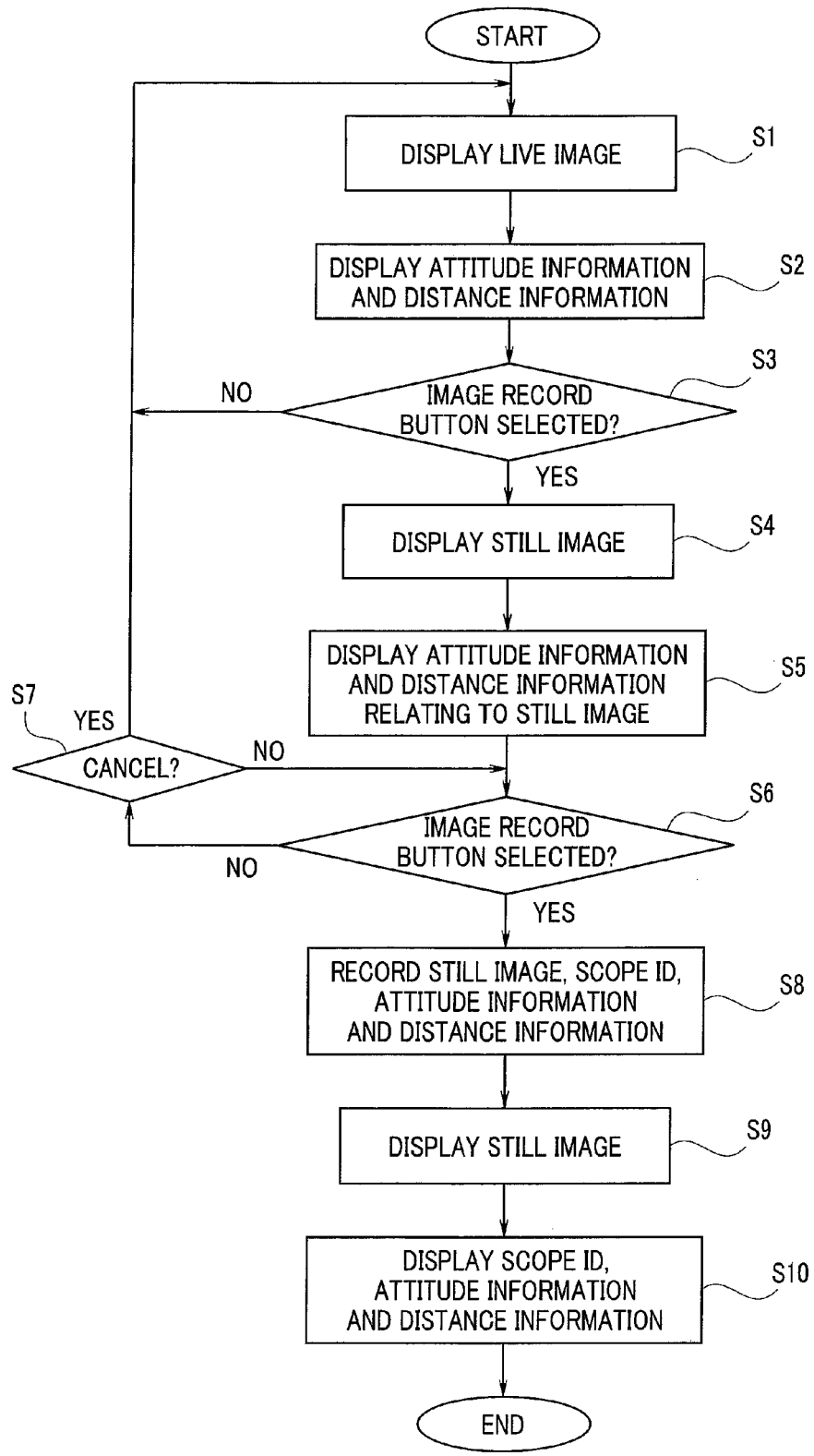
FIG. 9 is a flowchart showing an example of a flow of recording processing according to the first embodiment when the borescope 11 is inserted and an endoscopic image is displayed and recorded.
Figure 10:
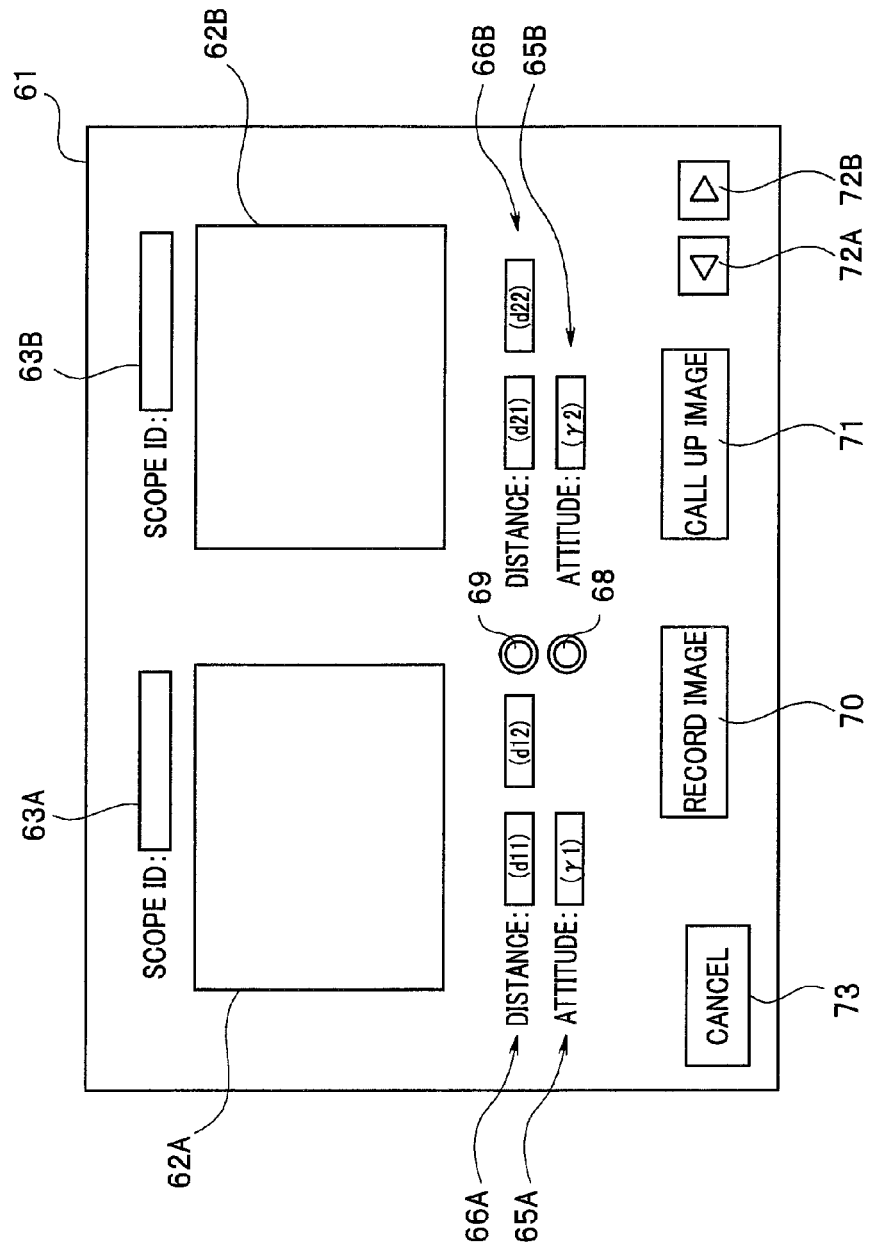
FIG. 10 is a diagram showing an example of a graphical user interface (GUI) displayed on the screen of an LCD 55 of the PC 12 according to the first embodiment.

FIG. 9 is a flowchart showing an example of a flow of recording processing when the borescope 11 is inserted and an endoscopic image is displayed and recorded. A program for recording processing shown in FIG. 9 is stored in the ROM 52 in the PC 12 and is read out and executed by the CPU 51. FIG. 10 is a diagram showing an example of a graphical user interface (GUI) displayed on the screen of the LCD 55 of the PC 12.

The configuration of the GUI (graphical user interface) displayed on the screen of the LCD 55 of the PC 12 at the time of blade inspection will first be described with reference to FIG. 10.

As shown in FIG. 10, a GUI 61 displayed on the screen of the LCD 55 of the PC 12 is a graphical user interface including two image display portions 62A and 62B in which inspection images are displayed, a scope ID display portions 63A and 63B in which scope IDs are displayed, two attitude information display portions 65A and 65B in which attitude information is displayed, and two distance information display portions 66A and 66B in which distance information is displayed.

The GUI 61 further includes match indicators 68 and 69 each of which indicates a match between information items in one of two sorts of information, an image record button 70, an image call-up button 71, a backward button 72A, a forward button 72B, and a cancel button 73.

The image display portion 62A is a display area in which a live inspection image in current inspection received from the borescope 11 is displayed. The image display portion 62B is a display area in which a still image from inspection images recorded in the HDD 54 provided as a storage unit is displayed.

The scope ID display portions 63A and 63B are each a display area in which the scope ID for the borescope 11 when the corresponding one of inspection images displayed in the image display portions 62A and 62B is being obtained or was obtained is displayed.

The attitude information display portions 65A and 65B are each a display area in which attitude information about the borescope 11 produced when the corresponding one of inspection images respectively displayed in the image display portions 62A and 62B was obtained is displayed. The attribute information includes the angle of rotation γ about the axis, which angle is calculated from the outputs from the acceleration sensor 27. The attitude information display portion 65A has a display area in which the angle of rotation γ1 determined when an inspection image displayed in the image display portion 62A is being obtained or was obtained is displayed. The attitude information display portion 65B also has display area in which the angle of rotation γ2 determined when an inspection image displayed in the image display portion 62B was obtained is displayed.

The distance information display portions 66A and 66B are each a display area in which distance information obtained from the outputs from the two distance sensors 31a and 31b of the borescope 11 when the corresponding one of inspection images displayed in the image display portions 62A and 62B was obtained is displayed. The distance information is two distances d1 and d2 calculated and transmitted by the control unit 41 based on the outputs from the two distance sensors 31a and 31b. The distance information display portion 66A has two display areas in which two distances d11 and d12 determined when an inspection image displayed in the image display portion 62A is being obtained or was obtained are displayed. The distance information display portion 66B has two display areas in which two distances d21 and d22 determined when an inspection image displayed in the image display portion 62B was obtained are displayed. The distances d11 and d21 correspond to the distance d1 in FIG. 3, and the distances d21 and d22 correspond to the distance d2 in FIG. 3.

The match indicator 68 is a display portion that indicates a match between attitude information produced when an inspection image in still image form displayed in the image display portion 62B was obtained and attitude information about a live inspection image displayed in the image display portion 62A, as described below. A match between the two groups of attitude information with an error within a predetermined error range is indicated, for example, by changing the luminance or the color of the match indicator 68. Also, the match indicator 68 indicates, when red in color, that there is no match between the attitude relating to a still image and the attitude relating to a live image. When green in color, the match indicator 68 indicates that there is a match between the attitude relating to a still image and the attitude relating to a live image. Accordingly, a match between the two groups of attitude information implicates not only a perfect match between the two groups of attitude information but also a match with an error within the predetermined error range.

The match indicator 69 is a display portion that indicates a match between distance information produced when an inspection image in still image form displayed in the image display portion 62B was obtained and distance information about a live inspection image displayed in the image display portion 62A, as described below. A match between the two groups of distance information with an error within a predetermined error range is indicated, for example, by changing the luminance or the color of the match indicator 69. Accordingly, a match between the two groups of distance information implicates not only a perfect match between the two groups of distance information but also a match with an error within the predetermined error range. Also, the match indicator 69 indicates, when red in color, that there is no match between distance information about a still image and distance information about a live image. When green in color, the match indicator 69 indicates that there is a match between distance information relating to a still image and distance information relating to a live image.

Note that the match indicator 68 may be not changed from red to green when a match occurs between attitude information about a live inspection image and attitude information produced when an inspection image in still image form displayed in the image display portion 62B was obtained; the match indicator 68 may be changed from red to a predetermined color, for example, yellow when attitude information about a live inspection image enters a predetermined distance range with respect to attitude information produced when an inspection image in still image form displayed in the image display portion 62B was obtained, and may be thereafter changed to green when a match occurs therebetween.

The colors of the match indicator 69 may also be changed in a similar way. The color of the match indicator 69 may be changed to a predetermined color, e.g., yellow when distance information about a live inspection image enters a predetermined value range with respect to distance information produced when an inspection image in still image form was obtained, and may be thereafter changed to green when a match occurs therebetween.

The image record button 70 is a button displayed on the LCD 55 and operated by being touched by a user when a still image from a live image displayed in the image display portion 62A is to be recorded, as described below.

The image call-up button 71 is a button displayed on the LCD 55 and operated by being touched by a user when a still image recorded in the HDD 54 is called up and displayed in the image display portion 62B, as described below.

The backward button 72A is a button displayed on the LCD 55 and operated, when a plurality still images that are recorded in the HDD 54 are called up, to display the still image in the image display portion 62B by scrolling back from one image to another in predetermined order, as described below.

The forward button 72B is a button displayed on the LCD 55 and operated, when a plurality still images that are recorded in the HDD 54 are called up, to display the still image in the image display portion 62B by scrolling forward from one image to another in predetermined order, as described below.

The cancel button 73 is a button used by a user as an inspector when the user cancels a command after selecting the command.

The GUI 61 shown in FIG. 10 is displayed on the LCD 55 of the PC 12, and a user inspects the blade B.

As shown in FIG. 9, the CPU 51 displays on the LCD 55 a live inspection image (hereinafter referred to as "live image"), which is a moving endoscopic image, based on the image signal received from the borescope 11 (S1). The live image is displayed in the image display portion 62A of the GUI 61. At this time, since the scope ID is also received from the control unit 41 in the borescope 11, the CPU 51 displays the scope ID in the scope ID display portion 63A.

The CPU 51 then displays, in the attitude information display portion 65A and the distance information display portion 66A, respectively, attitude information and position information received in real time (S2).

The CPU 51 determines whether or not the image record button 70 has been selected or touched (S3). If the image record button 70 has not been selected (S3: NO), the process returns to S1.

If the image record button 70 has been selected (S3: YES), the CPU 51 produces a still image from the received live image and displays the still image in the image display portion 62A (S4).

The CPU 51 then displays, in the attitude information display portion 65A and the distance information display portion 66A, respectively, the attitude information and position information produced when the still image displayed in the image display portion 62A was obtained (S5).

The CPU 51 determines whether or not the image record button 70 has been again selected or touched (S6). If the image record button 70 has not been selected (S6: NO), the CPU 51 determines whether or not the cancel button 73 has been selected (S7). If the cancel button 73 has been selected (S7: YES), the process returns to S1. If the cancel button 73 has not been selected, no processing is performed.

If the image record button 70 has been selected (S6: YES), the CPU 51 records, in the HDD 54 provided as a storage device, the still image displayed in the image display portion 62A, the scope ID, and the attitude information and the position information relating to the still image (S8). The scope ID, the attitude information and the position information are included as EXIF information for image data in the image data and recorded in the HDD 54.

The CPU 51 displays the recorded still image in the image display portion 62B (S9), and displays, in the scope ID display portion 63B, the attitude information display portion 65B and the distance information display portion 66B, respectively, the scope ID, the attitude information and the position information produced when the still image displayed in the image display portion 62B was obtained (S10).

The user can thus record a still image from an inspection image of the blade B in the engine E. The user can store a plurality of inspection images in the HDD 54 as a result of repeated execution of the process shown in FIG. 9.

For example, the process shown in FIG. 9 is performed by using the borescope 11A having a comparatively wide view angle to roughly inspect the blade B, and a still image containing an image of a flawed portion is first recorded. To observe or record by enlarging the flawed portion, the inspector draws out the borescope 11A from the access port AP and inserts through the access port AP the borescope 11B having a view angle narrower than that of the borescope 11A.

Figure 11:
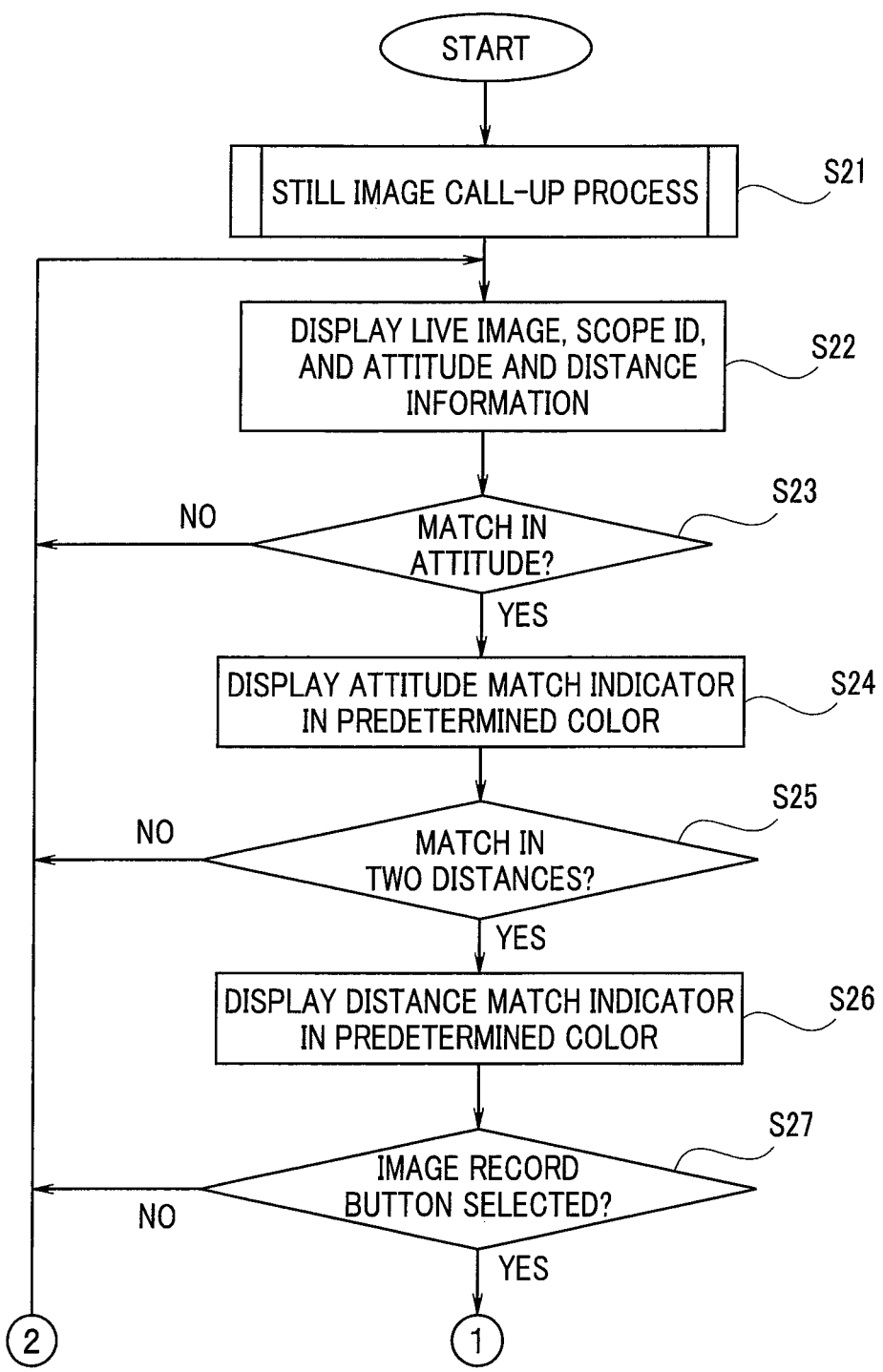
FIG. 11 is a flowchart showing an example of a flow of recording processing according to the first embodiment when a borescope 11 having a narrower view angle is inserted and an inspection image is displayed and recorded while referring to a recorded inspection image.
Figure 12:
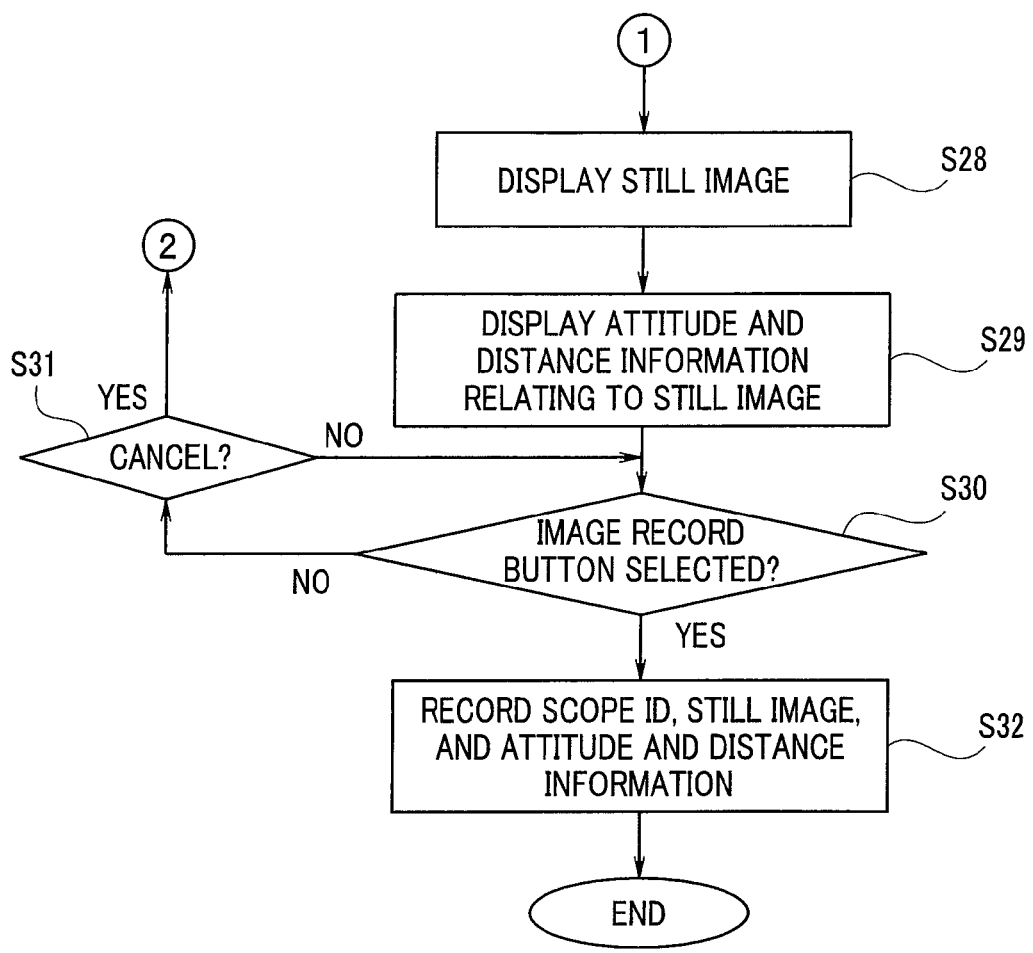
FIG. 12 is a flowchart showing an example of a flow of recording processing according to the first embodiment when a borescope 11 having a narrower view angle is inserted and an inspection image is displayed and recorded while referring to a recorded inspection image.

FIGS. 11 and 12 are flowcharts showing an example of a flow of recording processing for displaying and recording inspection images while inserting the borescope 11 having a narrower view angle and referring to recorded inspection images. A program for the recording process shown in FIGS. 11 and 12 is stored in the ROM 52 and is read out and executed by the CPU 51 in the PC 12.

When the image call-up button 71 of the GUI 61 is selected or touched by the inspector, the process shown in FIGS. 11 and 12 is executed.

The CPU 51 first executes an image call-up process (S21). A first inspection image, e.g., the earliest in the past in a time series from the plurality of inspection images recorded in the HDD 54 is displayed in the image display portion 62B. The user can select a desirable one of the plurality of inspection images recorded in the HDD 54 and display the selected inspection image in the image display portion 62B by using the forward button 72B and the backward button 72A.

When the inspection image selected by the user is displayed in the image display portion 62B, the scope ID, the attitude information and the position information relating to the inspection image are displayed in the scope ID display portion 63B, the attitude information display portion 65B and the distance information display portion 66B, respectively.

The user can thus display the recorded inspection image and the scope ID, the attitude information and the position information relating to the recorded inspection image in the GUI 61.

While the user inserts the borescope 11B in the engine E, the CPU 51 displays in the scope ID display portion 63A the scope ID received from the borescope 11B, displays a live image in the image display portion 62A, and displays the attitude information and position information relating to the live image in the attitude information display portion 65A and the distance information display portion 66A, respectively, in real time (S22). When the borescope 11B is moved, not only the live image displayed in the display portion 62A but also the display contents in the attitude information display portion 65A and the distance information display portion 66A are changed in real time.

First, the user moves the distal end portion of the insertion section 11a of the borescope 11B by pushing slowly toward the axis of rotation Ax, and keeps the borescope 11B at a predetermined position. While keeping the borescope 11B at the position, the user changes the attitude of the borescope 11B, i.e., the angle of rotation γ about the axis. The user changes the attitude of the borescope 11B while checking whether or not the match indicator 68 is changed from red to green, and stops the attitude changing operation when the match indicator 68 is changed from red to green.

The CPU 51 therefore determines whether there is a match between the attitude determined when the inspection image in still image form displayed in the image display portion 62B was obtained and the attitude of the borescope 11B with which the current live image is being obtained (S23). "A match between the attitudes" refers to a match in angle of rotation.

If there is no match between the two attitudes (S23: NO), the process returns to S22. Processing in S23 constitutes an attitude comparison section that makes a comparison between the attitude (the angle of rotation γ1 in the present embodiment) detected by the acceleration sensor 27 of the borescope 11B and the attitude (the angle of rotation γ2 in the present embodiment) relating to the inspection image stored in the HDD 54 and displayed in the image display portion 62B. That is, the two attitudes are compared in a state where the insertion axis of the insertion section 11a of the borescope 11A when the attitude of the borescope 11A is detected and the insertion axis of the insertion section 11a of the borescope 11B coincide with each other.

Note that in determination in S23 as to whether or not there is a match between the two attitudes, it is determined that there is a match between the two attitudes if the angle of rotation γ1 calculated from the outputs from the acceleration sensor 27 of the borescope 11B with which the current live image is being obtained fall within predetermined allowable ranges with respect to the angle of rotation γ2 calculated from the outputs from the acceleration sensor 27 with respect to the inspection image displayed in the image display portion 62B. For example, if the angle of rotation γ1 of the borescope 11B is within a range from (γ2−Δk2) to (γ2+Δk2) with respect to the borescope 11A, it is determined that there is a match between the two attitudes.

If there is a match between the two attitudes (S23: YES), the CPU 51 gives the match indicator 68 an indication in a predetermined color, green in the present embodiment (S24). When the color of the match indicator 68 is green, the user recognizes the match between the attitude determined when the inspection image displayed in the image display portion 62B was obtained and the attitude of the borescope 11B with which the current live image is being obtained.

Thus, processing in S24 constitutes a match output section that, based on the result of comparison in S23, outputs match information indicating that there is a match between the attitude (the angle of rotation γ1 in the present embodiment) detected by the acceleration sensor 27 of the borescope 11B and the attitude (the angle of rotation γ2 in the present embodiment) relating to the inspection image stored in the HDD 54 and displayed in the image display portion 62B. With the output of the predetermined match information as a result of processing in S24, the indication (color in the present embodiment) with the match indicator 68, which is a predetermined mark displayed on the LCD 55 provided as a display device, is changed.

Next, the user moves the distal end portion of the insertion section 11a of the borescope 11B by pushing slowly toward the axis of rotation Ax while holding the borescope 11B so that the attitude of the borescope 11B is not changed. The user changes the position of the distal end portion of the insertion section 11a while checking whether or not color of the match indicator 69 is changed from red to green and while pushing in the borescope 11B, and stops the inserting operation when the color of the match indicator 69 is changed from red to green.

The CPU 51 therefore determines whether there is a match between the two distances d1 and d2 determined when the inspection image in still image form displayed in the image display portion 62B was obtained and the two distances d1 and d2 of the borescope 11B with which the current live image is being obtained (S25).

If there is a match between the two groups of the distances (S25: YES), there is a match between the position of the image pickup optical center Pc of the insertion section 11a of the borescope 11A determined when the inspection image displayed in the image display portion 62B was obtained and the position of the image pickup optical center Pc of the borescope 11B with which the current live image is being obtained.

Processing in S25 constitutes a distance comparison section that makes a comparison between the two distances d1 and d2 detected by the two distance sensors 31a and 31b of the borescope 11B and the two distances d1 and d2 relating to the inspection image stored in the HDD 54 and displayed in the image display portion 62B.

The position of the distal end portion of the insertion section 11a will be described below.

Figure 14:
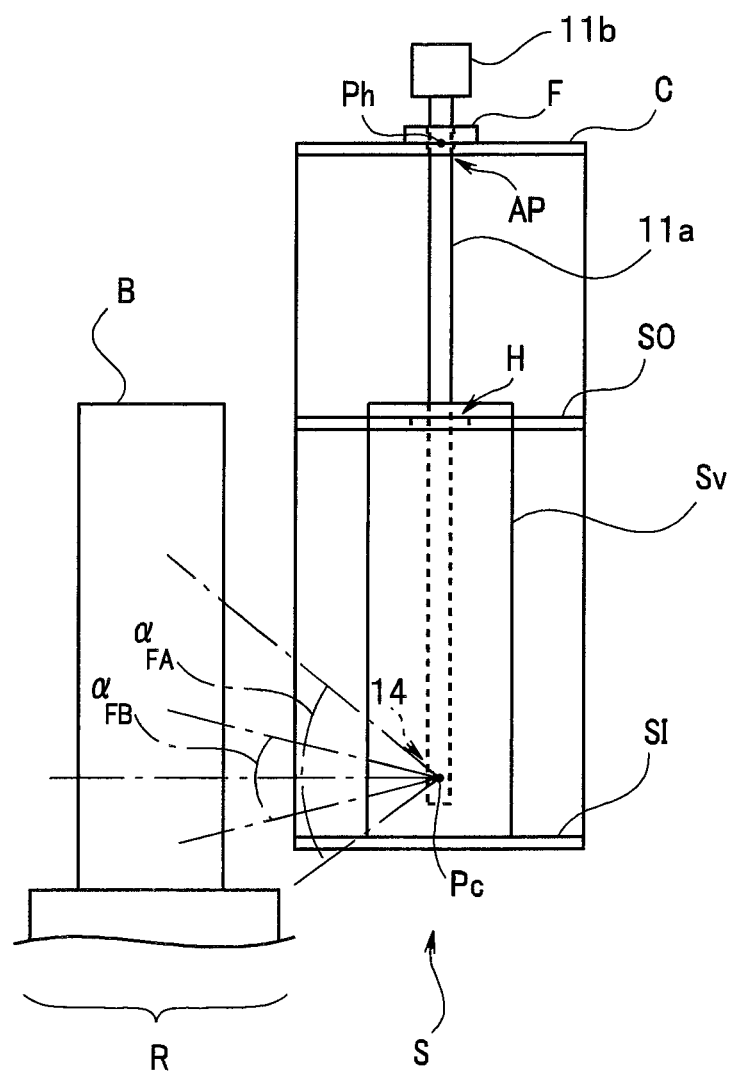
FIG. 14 is diagram for explaining the state of the insertion section 11a according to the first embodiment when one stator vane Sv is seen along a direction perpendicular to an axis of rotation Ax of a rotor in explanation of a state where the insertion section 11a is inserted in the casing C of the engine E.
Figure 15:
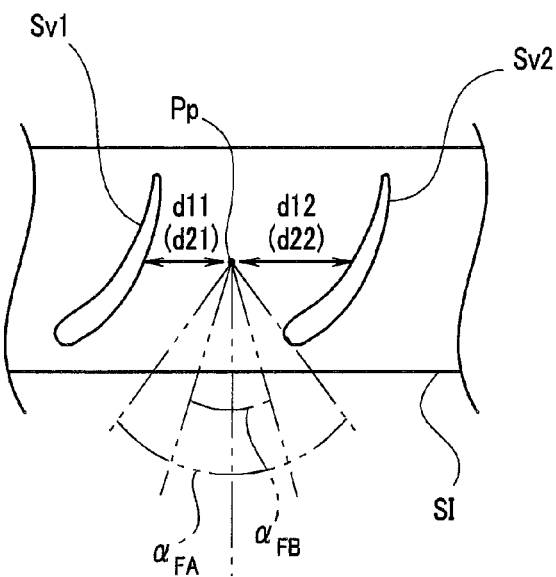
FIG. 15 is a schematic diagram for explaining a position for the image pickup optical center of a distal end portion of the insertion section 11a according to the first embodiment.

FIGS. 13 to 16 are diagrams for explaining the position of the distal end portion of the insertion section 11a. FIG. 13 is a perspective view of a portion of the stator S for explaining a state where the insertion section 11a is inserted in the casing C of the engine E. FIG. 14 is a diagram for explaining the state of the insertion section 11a when one stator vane Sv is seen along a direction perpendicular to the axis of rotation Ax of the rotor in explanation of a state where the insertion section 11a is inserted in the casing C of the engine E. FIG. 15 is a schematic diagram for explaining a position for the image pickup optical center of the distal end portion of the insertion section 11a.

As shown in FIGS. 13 and 14, the fixing implement F is attached to the access port AP provided in the casing C, and the insertion section 11a is passed through the insertion hole in the fixing implement F. The insertion section 11a is inserted toward an inner shroud SI by being passed through a hole H provided in an outer shroud SO in the stator S.

In the stator S, a plurality of stator vanes Sv are provided between the outer shroud SO and the inner shroud SI along the circumferential directions of the cylindrical outer and inner shrouds SO and SI. The insertion section 11a passed through the hole H is inserted between the two stator vanes Sv1 and Sv2.

Referring back to FIG. 11, in S25, the CPU 51 executes in real time the determination as to whether there is a match between the two distance values d11 and d12 detected by the two distance sensors 31a and 31b and the two distance values d21 and d22 displayed in the distance information display portion 66B. That is, after S24, the CPU 51 determines whether there is a match between the two groups of distances (S25).

Note that in determination in S25 as to whether or not there is a match between the two groups of distances, it is determined that there is a match between the two groups of distances if the two distance values d11 and d12 detected by the two distance sensors 31a and 31b of the borescope 11B with which the current live image is being obtained fall within predetermined allowable ranges with respect to the distances d21 and d22 relating to the inspection image displayed in the image display portion 62B. For example, if the two distance values d11 and d12 are within a range from (d21−Δk1) to (d21+Δk1) and a range from (d22−Δk1) to (d22+Δk1), respectively, it is determined that there is a match between the two groups of distances.

If there is no match between the two groups of distances (S25: NO), the process returns to S22. If there is a match between the two groups of distances (S25: YES), the CPU 51 gives the match indicator 69 an indication in a predetermined color, green in the present embodiment (S26).

Figure 16:
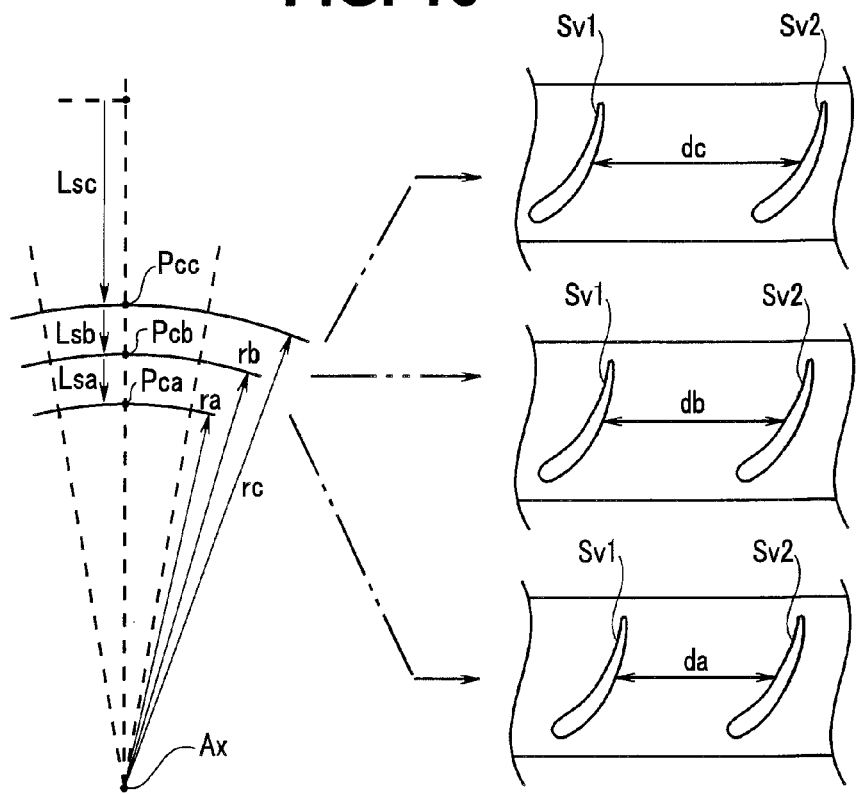
FIG. 16 is a diagram for explaining the relationship between the position of an image pickup optical center Pc of the insertion section 11a as seen in a direction along the axis of rotation Ax and two distance values d11 and d12 according to the first embodiment.

FIG. 16 is a diagram for explaining the relationship between the position of the image pickup optical center Pc of the insertion section 11a as seen in a direction along the axis of rotation Ax and the two distance values d11 and d12.

As shown in FIG. 16, the distance between two stator vanes Sv1 and Sv2 is changed between a state where the position of the image pickup optical center Pc is closer to the axis of rotation Ax and a state where the position of the image pickup optical center Pc is remoter from the axis of rotation Ax.

For example, in comparison between when the image pickup optical center Pc is positioned at an image pickup optical center Pca at a distance ra from the axis of rotation Ax and when the image pickup optical center Pc is positioned at an image pickup optical center Pcb at a distance rb remoter than the image pickup optical center Pca from the axis of rotation Ax, a distance da between central portions of the two stator vanes Sv1 and Sv2 at the image pickup optical center Pca is shorter than a distance db between central portions of the two stator vanes Sv1 and Sv2 at the image pickup optical center Pcb. This is because the stator vanes Sv1 and Sv2 respectively extend radially from the center of the axis of rotation Ax.

Similarly, in comparison between when the image pickup optical center Pc is positioned at the image pickup optical center Pcb at the distance rb from the axis of rotation Ax and when the image pickup optical center Pc is positioned at an image pickup optical center Pcc at a distance rc further remoter than the image pickup optical center Pcb from the axis of rotation Ax, the distance db between the central portions of the two stator vanes Sv1 and Sv2 at the image pickup optical center Pcb is shorter than a distance dc between central portions of the two stator vanes Sv1 and Sv2 at the image pickup optical center Pcc.

Conversely, if the insertion length L is increased, the distance between the two stator vanes Sv1 and Sv2 is reduced. As shown in FIG. 16, the distance db between the central portions of the stator vanes Sv1 and Sv2 when the insertion length L is an insertion length Lsb is longer than the distance da between the central portions of the stator vanes Sv1 and Sv2 when the insertion length L is an insertion length Lsa longer than the insertion length Lsb. Similarly, the distance dc between the central portions of the stator vanes Sv1 and Sv2 when the insertion length L is an insertion length Lsc is longer than the distance db between the central portions of the two stator vanes Sv1 and Sv2 when the insertion length L is an insertion length Lsb longer than the insertion length Lsc.

The insertion length L is uniquely determined by the distances to the two stator vanes Sv detected with the two distance sensors 31a and 31b in the insertion section 11a positioned between the two stator vanes Sv. Accordingly, when a match occurs between two distance values d21 and d22 detected with the two distance sensors 31a and 31b in the preceding inspection and distance values d11 and d12 detected with the two distance sensors 31a and 31b of the borescope 11B, the insertion length L is equal to the insertion length L at the time of the preceding inspection.

That is, the distance L is detected based on the two distances d1 and d2 detected with the distance sensors 31a and 31b, which are provided in the borescope 11B, and which detect the two distances d1 and d2 from the insertion section 11a to two objects in two directions perpendicular to the axis of the insertion section 11a and opposite to each other. That is, the distance sensors 31a and 31b constitute an insertion length detection unit.

If a match occurs between the two groups of distances (S25: YES), the CPU 51 gives the match indicator 69 an indication in a predetermined color, green in the present embodiment (S26). When the color of the match indicator 69 is green, the user can recognize the match between the two distance values d21 and d22 determined when the inspection image displayed in the image display portion 62B was obtained and the distance values d11 and d12 of the borescope 11B with which the current live image is being obtained.

Processing in S26 constitutes a match output section that, based on the result of comparison in S25, outputs match information indicating that there is a match between the two distance values d1 and d2 detected by the two distance sensors 31a and 31b of the borescope 11B and the two distance values d1 and d2 relating to the inspection image stored in the HDD 54 and displayed in the image display portion 62B. With the output of the predetermined match information as a result of processing in S26, the indication (color in the present embodiment) with the match indicator 69, which is a predetermined mark displayed on the LCD 55 provided as a display device, is changed.

In S24 and S26 described above, a match between the angles of rotation γ and a match between the two distances d1 and d2 are indicated by the two match indicators 68 and 69. The user can therefore observe an enlarged image of the blade B at the same position in the same viewing direction as at the time of obtaining the still image.

After processing in S26, the CPU 51 determines whether or not the image record button 70 has been selected or touched (S27). If the image record button 70 has not been selected (S27: NO), the process returns to S22.

If the image record button 70 has been selected (S27: YES), as shown in FIG. 12, the CPU 51 produces a still image from the received live image and displays the still image in the image display portion 62A (S28).

The CPU 51 displays, in the attitude information display portion 65A and the distance information display portion 66A, respectively, the attitude information and position information determined when the still image displayed in the image display portion 62A was obtained (S29).

The CPU 51 determines whether or not the image record button 70 has been again selected or touched (S30). If the image record button 70 has not been selected (S30: NO), the CPU 51 determines whether or not the cancel button 73 has been selected (S31). If the cancel button 73 has been selected (S31: YES), the process returns to S22. If the cancel button 73 has not been selected, no processing is performed.

If the image record button 70 has been selected (S30: YES), the CPU 51 records, in the HDD 54 provided as a storage device, the still image displayed in the image display portion 62A, and the scope ID, the attitude information and the position information relating to the still image (S32).

As described above, the inspector can display on the LCD 55 a still image (enlarged still image) picked up at the same position and in the same direction as the position and direction of the image pickup optical center Pc set when the recorded inspection image was picked up, and can store the sill image in the HDD 54.

Note that in the present embodiment, the scope ID, the attitude information and the position information relating to the still image are recorded as EXIF information of the image data in the HDD 54. However, the scope ID, the attitude information and the position information may alternatively be recorded in a file such as shown in FIG. 17, separately from the file for the still image.

FIG. 17 is a diagram showing the data structure of a photographing information recording file. As shown in FIG. 17, a photographing information recording file 81 has, as recording items, an image ID, a scope ID, an angle of rotation, a first distance and a second distance. The image ID is an image ID for image data on a still image, i.e., information for association with image data on a still image.

The scope ID, angle of rotation, first distance and second distance correspond to the above-described scope ID, angle of rotation γ, distance d21 and distance d22. In S8, S22, and S32 described above, these sorts of information including the scope ID are recorded in or read out from the photographing information recording file 81.

In the present embodiment, as described above, a blade inspection apparatus and method can be implemented that enable, in blade inspection, observation of a blade at the same position and in the same viewing direction as at the time of image pickup from the blade already performed to obtain an inspection image.

Second Embodiment

The blade inspection apparatus in the first embodiment is constructed so that a blade can be observed at the same position and in the same viewing direction as at the time of taking a still image to be recorded, based on the two distances d1 and d2 and the angle of rotation γ. A blade inspection apparatus in a second embodiment is constructed so that a blade can be observed at the same position and in the same viewing direction as at the time of taking a still image to be recorded, based on the insertion length L and the angle of rotation γ.

In the first embodiment, by utilizing the fact that the insertion length L is uniquely determined by the distances to stator vanes Sv detected with the two distance sensors 31a and 31b in the insertion section 11a positioned between the two stator vanes Sv, insertion assistance is performed based on the two distances d1 and d2 and the angle of rotation γ next time the borescope is inserted. Accordingly, a match between the two distances d1 and d2 and angles of rotation γ is determined in the first embodiment.

On the other hand, in the second embodiment, insertion assistance is performed based on the insertion length L and the angle of rotation γ of the insertion section 11a next time the borescope is inserted. Accordingly, a match between the insertion lengths L and angles of rotation γ is determined in the second embodiment.

A blade inspection system according to the present embodiment will be described below. The configuration of the blade inspection system according to the present embodiment is substantially the same as that of the blade inspection system described in the description of the first embodiment. The same components as those described above are indicated by the same reference characters and the description for them will not be repeated. Description will be made mainly of different components.

(Configuration of Borescope)

Figure 18:
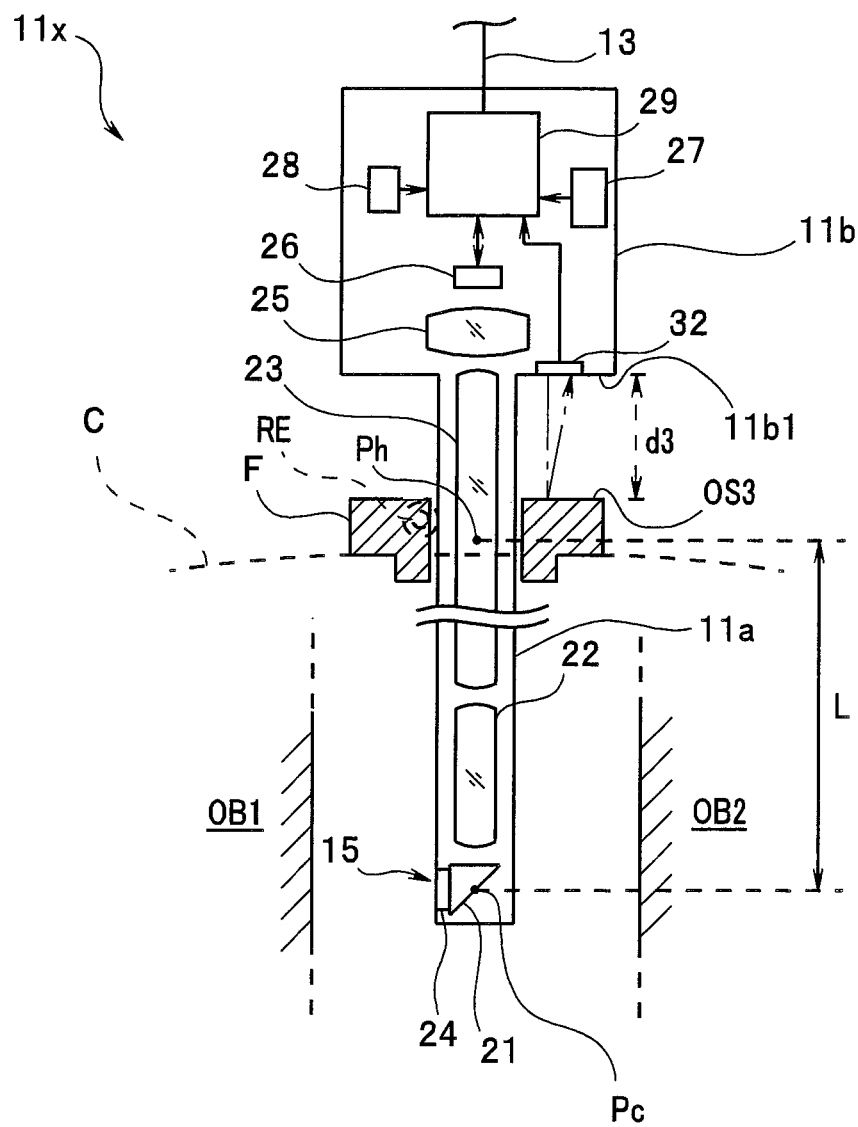
FIG. 18 is a diagram for explaining the configuration of a borescope 11x according to a second embodiment.

FIG. 18 is a diagram for explaining the configuration of a borescope 11x.

A distance sensor 32 is disposed in the grasping section 11b of the borescope 11x.

The acceleration sensor 27 is a three-axis acceleration sensor. The communication control unit 29 calculates the angle of rotation γ of the borescope 11x about the axis from outputs from the acceleration sensor 27. The distance sensor 32 is a sensor for detecting the distance to a surface of an object existing in such a position as to be opposed to the sensor. The distance sensor 32 is of the same configuration as the distance sensors 31a and 31b in the first embodiment. For example, the distance sensor 32 is a PSD distance sensor having a light source element that projects a spot of light and a position sensitive detector (PSD) element that detects the position of the centroid of a received spot of light. The PSD distance sensor detects the distance to an object by using the principle of triangulation.

The distance sensor 32 is provided on a surface 11b1 of the grasping section 11b on the insertion section 11a side (i.e., on the distal end side). As shown in FIG. 18, the distance sensor 32 detects a distance d3 from the surface 11b1 on the insertion section 11a side, i.e., on the distal end side, to a surface OS3 of the fixing implement F. That is, when the insertion section 11a is inserted into the engine E, the distance sensor 32 outputs a detection signal according to the distance to the surface OS3 of the fixing implement F. The distance sensor 32 measures the distance, for example, in a range of about 300 mm at the maximum. The communication control unit 29 calculates the insertion length L of the insertion section 11a based on the detection output from the distance sensor 32, as described below.

The distance sensor 32 and the communication control unit 29 are provided in the borescope 11x, which is the endoscope having the insertion section 11a, and constitute an insertion length detection section that detects the insertion length L of the insertion section 11a when the insertion section 11a is inserted from the access port AP, which is a hole provided in the casing C in which the rotor R is housed. That is, the distance sensor 32 detects the distance d3 between the grasping section 11b of the borescope 11x and the fixing implement F that supports and fixes the borescope 11x, and the insertion length L of the borescope 11x is detected based on the detected distance d3.

Note that while a PSD distance sensor is used as distance sensor 32 in the present embodiment, the system may alternatively be such that an encoder RE such as a roller encoder is provided on the fixing implement F, for example, as indicated by a broken line in FIG. 18; an output from the roller encoder RE is supplied to the PC 12 through a signal line led out from the roller encoder RE; and the insertion length L of the insertion section 11a is calculated from the output from the roller encoder RE in the PC 12.

The detection signal from the distance sensor 32, the image signal from the CCD 26, the respective detection signals from the acceleration sensor 27 and the scope ID signal from the ID storage unit 28 are inputted to the communication control unit 29.

Figure 19:
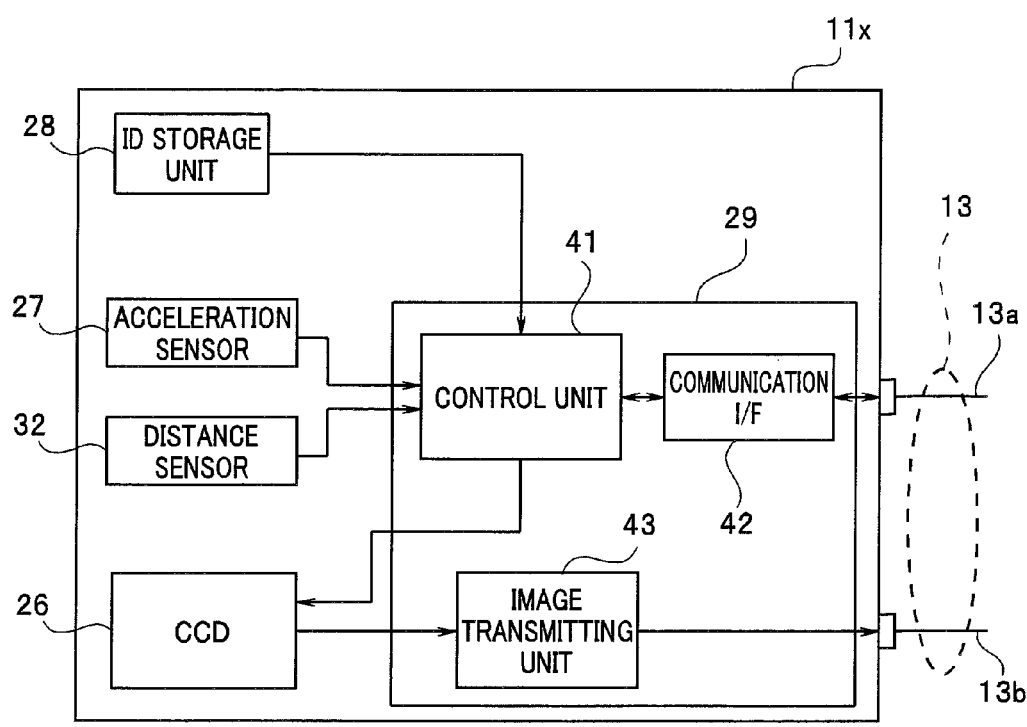
FIG. 19 is a block diagram showing the circuit configuration of the borescope 11x according to the second embodiment.

FIG. 19 is a block diagram showing the circuit configuration of the borescope 11x.

The distance sensor 32 is connected to the control unit 41.

Accordingly, the control unit 41 is supplied the scope ID of the borescope 11 from the ID storage unit 28 and the detection signals from the acceleration sensor 27 and the distance sensor 32.

The control unit 41 calculates the insertion length L based on the distance d3 corresponding to the detection signal from the distance sensor 32.

The center point Ph of the fixing implement F is determined in advance from the shape of the fixing implement F. Further, the positional relationship between the distance sensor 32 and the image pickup optical center. Pc is determined in advance. The control unit 41 can therefore calculate the insertion length L from the distance d3 corresponding to the detection signal from the distance sensor 32 even when the insertion section 11a is moved along the axial direction.

Note that the insertion length L may be determined from points other than the center point Ph and the image pickup optical center Pc.

The control unit 41 calculates the angle of rotation γ of the borescope 11x about the axis as attitude information about the borescope 11x based on the detection signals from the acceleration sensor 27.

The control unit 41 outputs in real time the insertion length L and attitude information calculated based on the detection signals from the respective sensors to the PC 12 through the communication I/F 42.

In other respects, the configuration and the operation of the borescope 11x are the same as those described in the description of the first embodiment.

The configuration of the PC 12 is also the same as the configuration described in the description of the first embodiment.

(Procedure of Inspection)

Also in the present embodiment, a user as an inspector who inspects blades first performs an overall inspection of the blades by using a borescope 11xA of a wide view angle. The user thereafter performs a detailed inspection by using a borescope 11xB of a narrow view angle and by displaying an enlarged image of a defective portion found in the preceding inspection.

The configurations of the borescopes 11xA and 11xB in the present embodiment are identical in external shape and size to each other.

The view angle $\alpha_{FA}$ of the borescope 11xA is larger than the view angle $\alpha_{FB}$ of the borescope 11xB.

Further, the viewing direction angle $\alpha_{DA}$ from the axial direction of the insertion section 11a of the borescope 11xA is equal to the viewing direction angle $\alpha_{DB}$ from the axial direction of the insertion section 11a of the borescope 11xB. Note that each of the viewing direction angle $\alpha_{DA}$ and the viewing direction angle $\alpha_{DB}$ in the present embodiment is 90 degrees.

That is, the borescope 11xA has the insertion section 11a, the acceleration sensor that detects the same attitude as that detected by the acceleration sensor 27 of the borescope 11xB, and the distance sensor 32 that detects the same distance d3 as the borescope 11xB.

As described above, the respective parameters of the two borescopes 11xA and 11xB other than the view angles in the image pickup optical systems are equal to each other. Therefore, the image pickup optical centers Pc of the two borescopes 11xA and 11xB in image pickup from an object coincide with each other when the borescopes 11xA and 11xB have the same insertion amounts L and the same viewing directions.

(Function)

The operation of the blade inspection system 1 will be described.

Figure 20:
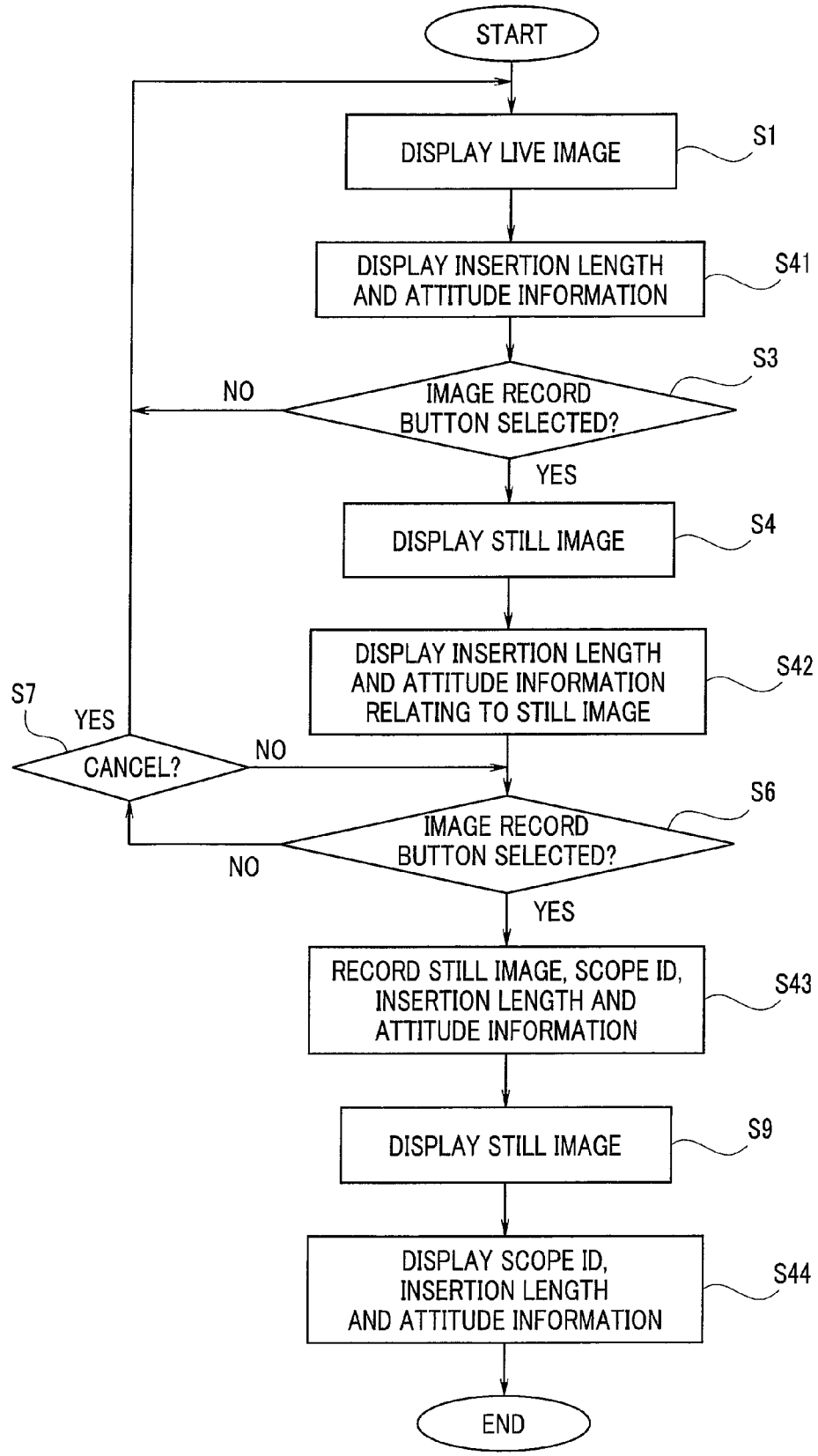
FIG. 20 is a flowchart showing an example of a flow of recording processing according to the second embodiment when the borescope 11x is inserted and an endoscopic image is displayed and recorded.
Figure 21:
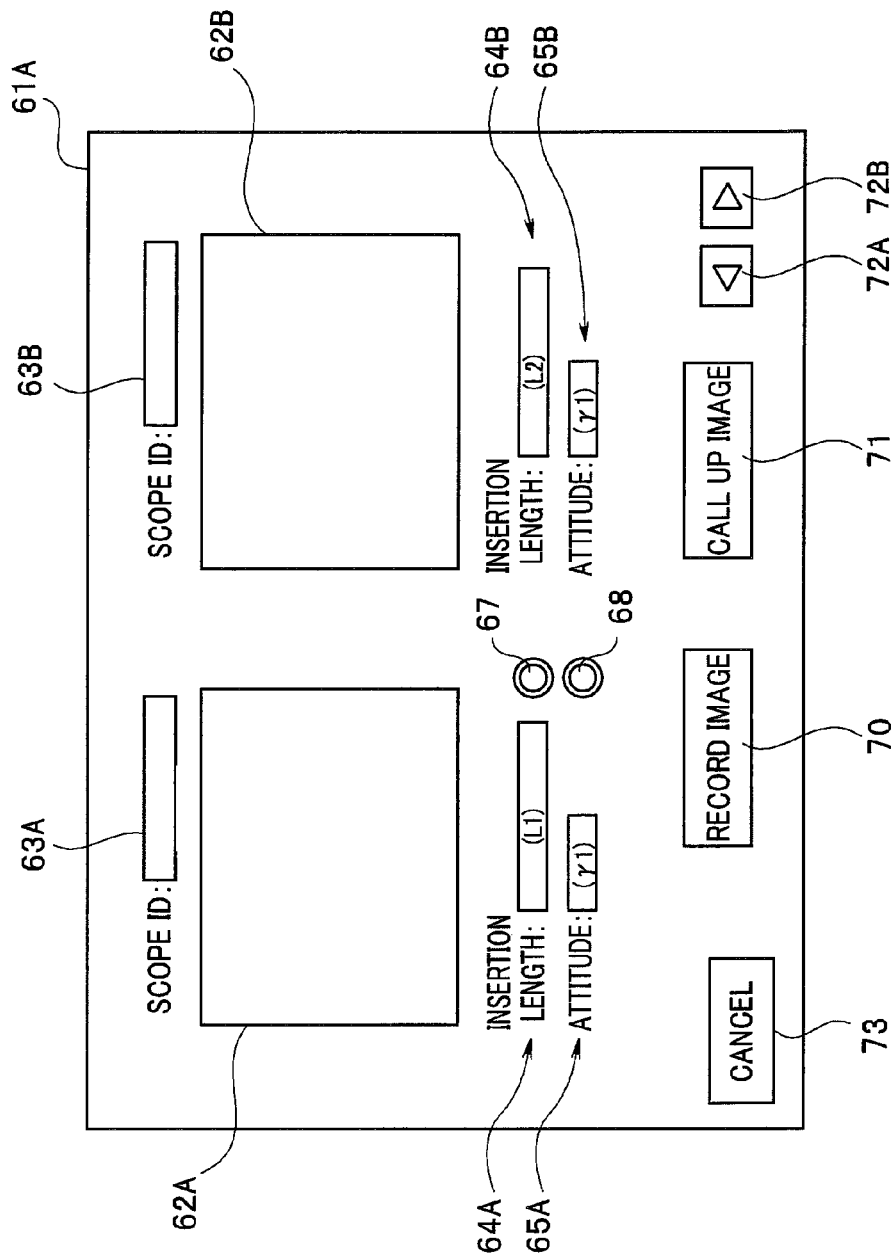
FIG. 21 is a diagram showing an example of a graphical user interface (GUI) displayed on the screen of an LCD 55 of a PC 12 according to the second embodiment.

FIG. 20 is a flowchart showing an example of a flow of recording processing when the borescope 11x is inserted and an endoscopic image is displayed and recorded. A program for recording processing shown in FIG. 20 is stored in the ROM 52 in the PC 12 and is read out and executed by the CPU 51. FIG. 21 is a diagram showing an example of a graphical user interface (GUI) displayed on the screen of the LCD 55 of the PC 12.

The configuration of the GUI (graphical user interface) displayed on the screen of the LCD 55 of the PC 12 at the time of blade inspection will first be described with reference to FIG. 21. In FIG. 21, the same components as those in FIG. 10 are indicated by the same reference characters and the description for them will not be repeated. Description will be made mainly of different components.

As shown in FIG. 21, a GUI 61A displayed on the screen of the LCD 55 of the PC 12 includes two insertion length information display portions 64A and 64B for indication of the insertion length and a match indicator 67 for indication of a match between information items.

The insertion length information display portions 64A and 64B are each a display area in which the insertion length L of the borescope 11x when an inspection image displayed in the image display portion 62A or 62B is being obtained or was obtained is displayed. The insertion length L is a value calculated by the control unit 41 of the borescope 11x based on the output from the distance sensor 32 and transmitted by the control unit 41. In the insertion length information display portions 64A, the insertion length L1 when an inspection image displayed in the image display portion 62A is being obtained or was obtained is displayed. In the insertion length information display portions 64B, the insertion length L2 when an inspection image displayed in the image display portion 62B was obtained is displayed.

The match indicator 67 is a display portion that indicates a match between the insertion length detected when an inspection image in still image form displayed in the image display portion 62B was obtained and the insertion length relating to a live inspection image displayed in the image display portion 62A. A match between the two insertion lengths with an error within a predetermined error range is indicated, for example, by changing the luminance or the color of the match indicator 67. Accordingly, a match between the two insertion lengths implicates not only a perfect match between the two insertion lengths but also a match with an error within the predetermined error range. In the present embodiment, the match indicator 67 indicates, when red in color, that there is no match between the insertion length relating to a still image and the insertion length relating to a live image. When green in color, the match indicator 67 indicates that there is a match between the insertion length relating to a still image and the insertion length relating to a live image.

Note that the match indicator 67 may be not changed from red to green when a match occurs between the insertion length relating to a live inspection image and the insertion length detected when an inspection image in still image form displayed in the image display portion 62B was obtained; the match indicator 67 may be changed from red to a predetermined color, for example, yellow when the insertion length relating to a live inspection image enters a predetermined distance range with respect to the insertion length detected when an inspection image in still image form displayed in the image display portion 62B was obtained, and may be thereafter changed to green when a match occurs therebetween.

The color of the other match indicator 68 may also be changed in a similar way. The color of the match indicator 68 may be changed to a predetermined color, e.g., yellow when attitude information relating to a live inspection image enters a predetermined value range with respect to attitude information produced when an inspection image in still image form was obtained, and may be thereafter changed to green when a match occurs therebetween.

Also in this case, a match between the two groups of attitude information implicates not only a perfect match between the two groups of attitude information but also a match with an error within the predetermined error range.

The GUI 61A shown in FIG. 21 is displayed on the LCD 55 of the PC 12 and the user inspects the blade B.

The same steps in FIG. 20 as those in FIG. 9 are indicated by the same step numbers and will be briefly described. First, as shown in FIG. 20, the CPU 51 displays on the LCD 55 a live image, which is a moving endoscopic image, based on the image signal received from the borescope 11x (S1). The live image is displayed in the image display portion 62A of the GUI 61A. At this time, since the scope ID is also received from the control unit 41 in the borescope 11x, the CPU 51 displays the scope ID in the scope ID display portion 63A.

The CPU 51 then displays, in the insertion length information display portion 64A and the attitude information display portion 65A, respectively, the insertion length and attitude information received in real time (S41).

The CPU 51 determines whether or not the image record button 70 has been selected or touched (S3). If the image record button 70 has been selected (S3: YES), the CPU 51 produces a still image from the received live image and displays the still image in the image display portion 62A (S4).

The CPU 51 then displays, in the insertion length information display portion 64A and the attitude information display portion 65A, respectively, the insertion length and attitude information produced when the still image displayed in the image display portion 62A was obtained (S42).

The CPU 51 determines whether or not the image record button 70 has been again selected or touched (S6). If the image record button 70 has been selected (S6: YES), the CPU 51 records, in the HDD 54 provided as a storage device, the still image displayed in the image display portion 62A, the scope ID, and the insertion length and the attitude information relating to the still image (S43). The scope ID, the insertion length and the attitude information are included as EXIF information in image data and recorded in the HDD 54.

The CPU 51 displays the recorded still image in the image display portion 62B (S9), and displays, in the scope ID display portion 63B, the insertion length information display portion 64B and the attitude information display portion 65B, respectively, the scope ID, the insertion length and the attitude information obtained when the still image displayed in the image display portion 62B was obtained (S44).

The user can thus record a still image from an inspection image of the blade B in the engine E. The user can store a plurality of inspection images in the HDD 54 as a result of repeated execution of the process shown in FIG. 20.

For example, the process shown in FIG. 20 is performed by using the borescope 11xA having a comparatively wide view angle to roughly inspect the blade B, and a still image containing an image of a flawed portion is first recorded. To observe or record by enlarging the flawed portion, the inspector draws out the borescope 11xA from the access port AP and inserts through the access port AP the borescope 11xB having a view angle narrower than that of the borescope 11xA.

Figure 22:
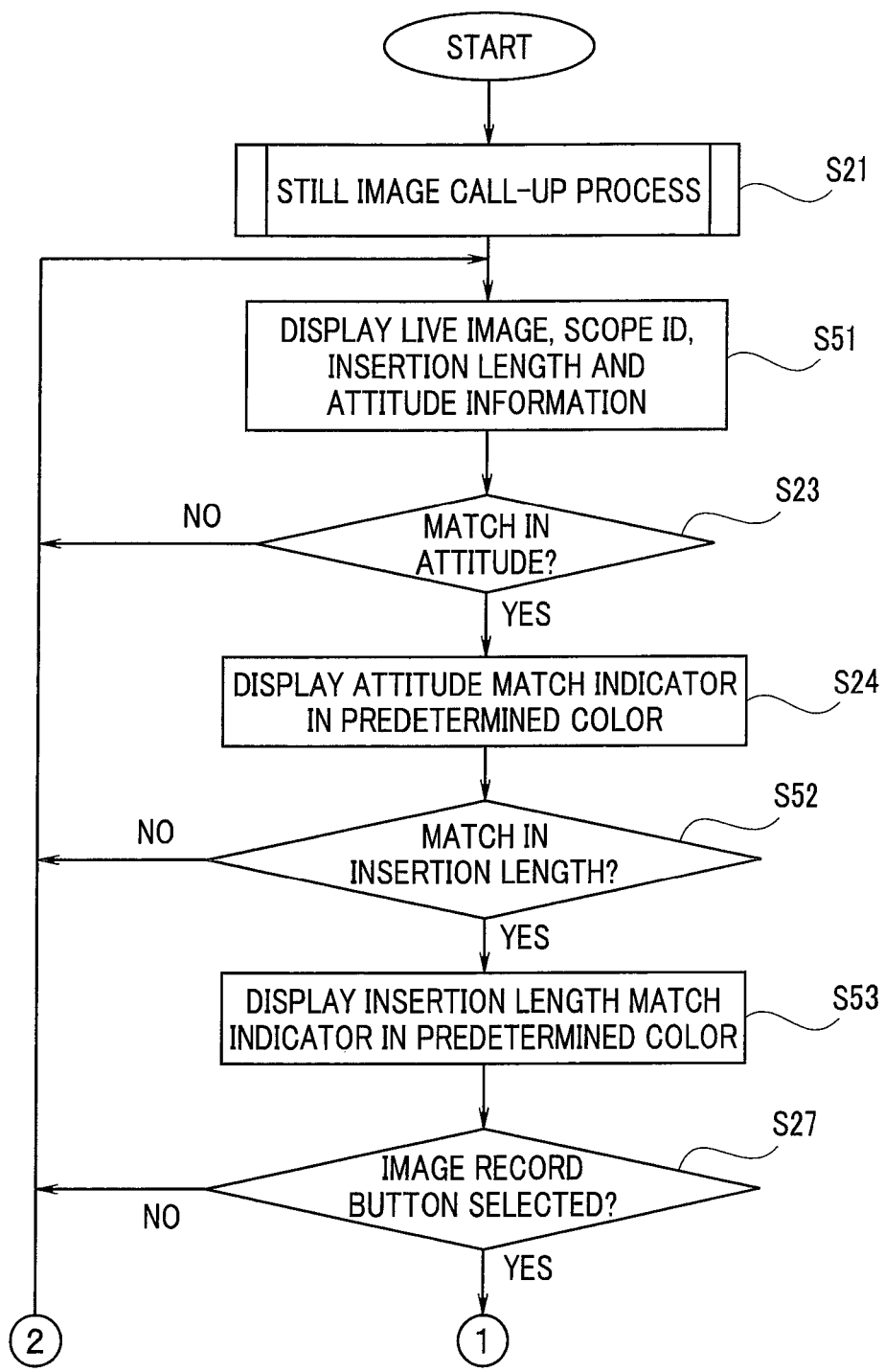
FIG. 22 is a flowchart showing an example of a flow of recording processing according to the second embodiment when a borescope 11 having a narrower view angle is inserted and an inspection image is displayed and recorded while referring to a recorded inspection image.
Figure 23:
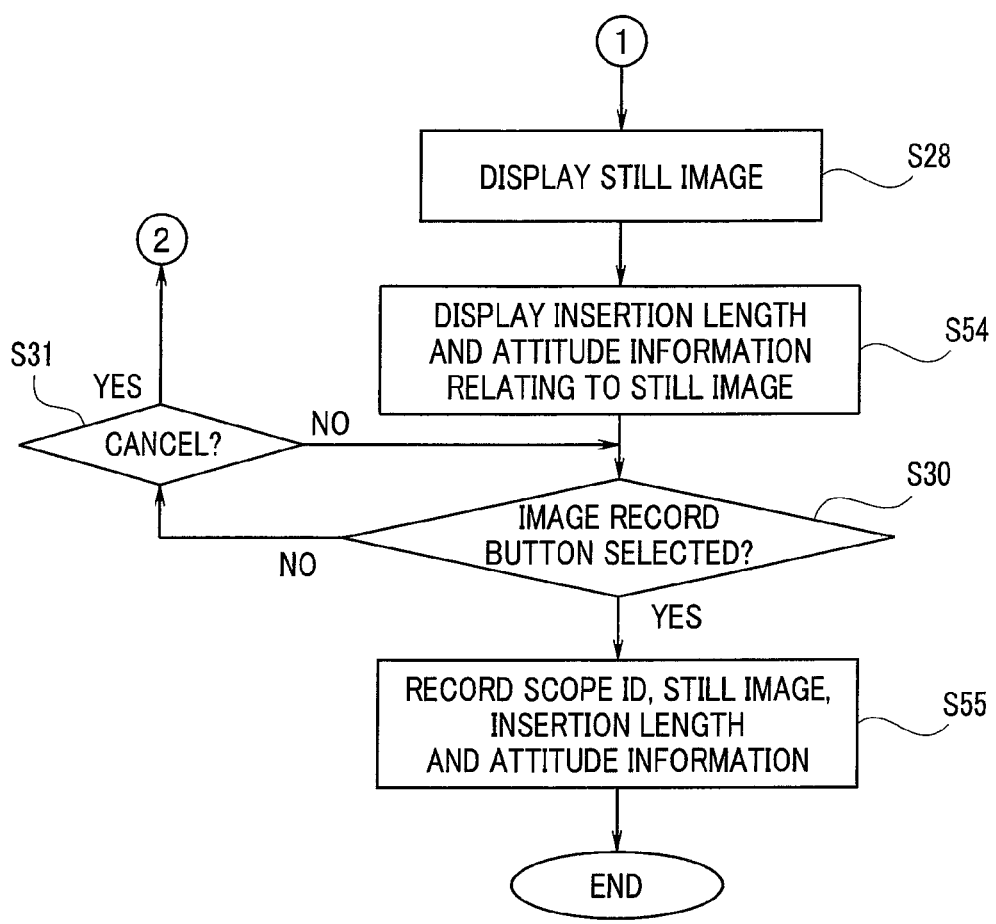
FIG. 23 is a flowchart showing an example of a flow of recording processing according to the second embodiment when a borescope 11 having a narrower view angle is inserted and an inspection image is displayed and recorded while referring to a recorded inspection image.

FIGS. 22 and 23 are flowcharts showing an example of a flow of recording processing for displaying and recording inspection images while inserting the borescope 11 having a narrower view angle and referring to recorded inspection images. A program for the recording process shown in FIGS. 22 and 23 is stored in the ROM 52 and is read out and executed by the CPU 51 in the PC 12.

When the image call-up button 71 of the GUI 61 is selected or touched by the inspector, the process shown in FIGS. 22 and 23 is executed. The same steps in FIGS. 22 and 23 as those in FIGS. 11 and 12 are indicated by the same step numbers and will be briefly described.

First, the CPU 51 executes an image call-up process (S21).

When an inspection image selected by the user is displayed in the image display portion 62B, the scope ID, the insertion length and attitude information relating to the inspection image are displayed in the scope ID display portion 63B, the insertion length information display portion 64B and the attitude information display portion 65B, respectively.

While the user inserts the borescope 11xB in the engine E, the CPU 51 displays in the scope ID display portion 63A the scope ID received from the borescope 11xB, displays a live image in the image display portion 62A, and displays the insertion length and attitude information relating to the live image in the insertion length information display portion 64A and the attitude information display portion 65A, respectively, in real time (S51). When the borescope 11xB is moved, not only the live image displayed in the display portion 62A but also the display contents in the insertion length information display portion 64A and the attitude information display portion 65A are changed in real time.

First, the user moves the distal end portion of the insertion section 11a of the borescope 11xB by pushing slowly toward the axis of rotation Ax, and keeps the borescope 11xB at a predetermined position. While keeping the borescope 11xB at the position, the user changes the attitude of the borescope 11xB, i.e., the angle of rotation about the axis. The user changes the attitude of the borescope 11xB while checking whether or not the match indicator 68 is changed from red to green, and stops the attitude changing operation when the match indicator 68 is changed from red to green.

The CPU 51 therefore determines whether there is a match between the attitude detected when the inspection image in still image form displayed in the image display portion 62B was obtained and the attitude of the borescope 11xB with which the current live image is being obtained (S23).

If there is a match between the two attitudes (S23: YES), the CPU 51 gives the match indicator 68 an indication in a predetermined color, green in the present embodiment (S24). From the state of the match indicator 68 in green, the user can recognize that there is a match between the attitude detected when the inspection image displayed in the image display portion 62B was obtained and the attitude of the borescope 11xB with which the current live image is being obtained.

Next, the user moves the distal end portion of the insertion section 11a of the borescope 11xB by pushing slowly toward the axis of rotation Ax while holding the borescope 11xB so that the attitude of the borescope 11xB is not changed. At this time, the CPU 51 determines whether or not there is a match between the insertion length L2 detected when the inspection image in still image form displayed in the image display portion 62B was obtained and the insertion length L1 of the borescope 11xB with which the current live image is being obtained (S52). If there is no match between the two insertion lengths (S52: NO), the process returns to S51. Processing in S52 constitutes an insertion length comparison section that makes a comparison between the insertion length L1 detected with the distance sensor 32 of the borescope 11xB and the insertion length L2 relating to the inspection image stored in the HDD 54 and displayed in the image display portion 62B.

That is, in the user's operation to insert the borescope 11xB so that the borescope 11xB advances toward an inner portion of the engine E, the user inserts the borescope 11xB in the engine E while checking whether or not the match indicator 67 is changed from red to green, and stops the inserting operation when the match indicator 67 is changed from red to green.

It is determined in S52 that there is a match between the two insertion lengths if the insertion length L1 of the borescope 11xB L1 with which the current live image is being obtained falls within a predetermined allowable range with respect to the insertion length L2. For example, if the insertion length L1 is within a range from (L2−Δk3) to (L2+Δk3), it is determined that there is a match between the two insertion lengths.

If there is a match between the two insertion lengths (S52: YES), the CPU 51 gives the match indicator 67 an indication in a predetermined color, green in the present embodiment (S53). When the color of the match indicator 67 is green, the user can recognize that there is a match between the insertion length L2 detected when the inspection image displayed in the image display portion 62B was obtained and the insertion length L1 of the borescope 11xB with which the current live image is being obtained. Accordingly, processing in S53 constitutes a match output section that, based on the result of comparison in S52, outputs match information indicating that there is a match between the insertion length L1 detected by the distance sensor 32 of the borescope 11xB and the insertion length L2 relating to the inspection image stored in the HDD 54 and displayed in the image display portion 62B. With the output of the predetermined match information as a result of processing in S53, the indication (color in the present embodiment) with the match indicator 67, which is a predetermined mark displayed on the LCD 55 provided as a display device, is changed.

In S24 and S53 described above, a match between the insertion lengths L and a match between the angles of rotation γ are indicated by the two match indicators 67 and 68. The user can therefore observe an enlarged image of the blade B at the same position in the same viewing direction as at the time of obtaining the still image.

After processing in S53, the CPU 51 determines whether or not the image record button 70 has been selected or touched (S27). If the image record button 70 has been selected (S27: YES), the CPU 51 produces a still image from the received live image and displays the still image in the image display portion 62A (S28).

The CPU 51 then displays, in the insertion length information display portion 64A and the attitude information display portion 65A, respectively, the insertion length and attitude information produced when the still image displayed in the image display portion 62A was obtained (S54).

The CPU 51 determines whether or not the image record button 70 has been again selected or touched (S30). If the image record button 70 has been selected (S30: YES), the CPU 51 records, in the HDD 54 provided as a storage device, the still image displayed in the image display portion 62A, the scope ID, and the insertion length and the attitude information relating to the still image (S55).

The inspector can thus display on the LCD 55 a still image (enlarged still image) picked up at the same position of the image pickup optical center Pc and in the same direction to the image pickup optical center Pc as at the time of picking up the inspection image to be recorded, and can store the still image in the HDD 54.

Note that in the present embodiment, the scope ID, the insertion length and the attitude information relating to the still image are recorded in the HDD 54 as EXIF information in image data on the still image. However, the scope ID, the insertion length and the attitude information may alternatively be recorded in a file such as shown in FIG. 24 separately from the file of the still image.

FIG. 24 is a diagram showing the data structure of a photographing information recording file. As shown in FIG. 24, a photographing information recording file 81A has an image ID, a scope ID, an insertion length and an angle of rotation as recording items.

The scope ID, insertion length and angle of rotation correspond to the above-described scope ID, insertion length L and angle of rotation γ, and these sorts of information including the scope ID are recorded in the photographing information recording file 81A or read out from the photographing information recording file 81A in the above S43, S51 and S55.

In the present embodiment, as described above, a blade inspection apparatus and method that enable, in blade inspection, observation of a blade at the same position and in the same viewing direction as at the time of image pickup from the blade already performed to obtain an inspection image.

In the above-described two embodiments, as described above, a blade inspection apparatus and method can be implemented that enable, in blade inspection, observation of a blade at the same position and in the same viewing direction as at the time of image pickup from the blade already performed to obtain an inspection image.

The present invention is not limited to the above-described embodiments. Various changes and modifications can be made in the described embodiments without departing from the gist of the invention.

What is claimed is:

1. A blade inspection apparatus for inspecting a plurality of blades periodically disposed on a periphery of a rotating shaft of a rotor of an engine and rotated on the rotating shaft, the apparatus comprising:
   a first insertion length detection sensor that detects a first insertion length of a first insertion section of a first endoscope when the first insertion section is inserted through a hole provided in a casing in which the rotor is housed;
   a first attitude detection sensor provided in the first endoscope, the first attitude detection sensor detecting a first attitude of the first insertion section;
   a storage that, when a still image of one of the blades picked up by a second endoscope having a second insertion section, a second insertion length detection sensor that detects a same insertion length as the first insertion length detected by the first insertion detection sensor, and a second attitude detection sensor that detects a same attitude as the first attitude detected by the first attitude detection sensor is obtained, stores a second insertion length of the second insertion section detected by the second insertion length detection sensor, and a second attitude of the second insertion section detected by the second attitude detection sensor;
   a processor that is configured to:
   make a comparison between the first insertion length detected by the first insertion length detection sensor and the second insertion length stored in the storage;
   make a comparison between the first attitude detected by the first attitude detection sensor and the second attitude stored in the storage in a state where an insertion axis of the second insertion section at a time of detection of the second attitude and an insertion axis of the first insertion section coincide with each other;
   output first match information indicating that there is a match between the first insertion length and the second insertion length based on a result of the comparison made therebetween; and
   output second match information indicating that there is a match between the first attitude and the second attitude based on a result of the comparison made therebetween.

2. The blade inspection apparatus according to claim 1, wherein the processor outputs the first match information and the second match information respectively to change indications with predetermined first and second marks, displayed on a display.

3. The blade inspection apparatus according to claim 1, wherein the first and second attitudes are determined by angles of rotation of the first and second insertion sections about the respective first and second insertion axes.

4. The blade inspection apparatus according to claim 1, wherein the first insertion length detection sensor is provided in the first endoscope, detects two first distances from the first insertion section to two objects in two directions perpendicular to the insertion axis of the first insertion section and opposite to each other, and detects the first insertion length.

5. The blade inspection apparatus according to claim 1, wherein the first insertion length detection sensor is provided in the first endoscope, detects a distance between a grasping section of the first endoscope and a fixing implement that supports and fixes the first endoscope, and detects the first insertion length.

6. The blade inspection apparatus according to claim 1, wherein the first insertion length detection sensor is an encoder provided on a fixing implement that supports and fixes the first endoscope, the encoder detecting the first insertion length of the first insertion section.

7. The blade inspection apparatus according to claim 4, wherein the two objects are stator vanes provided on a stator of the engine.

8. A blade inspection method of inspecting a plurality of blades periodically disposed on a periphery of a rotating shaft of a rotor of an engine and rotated on the rotating shaft, the method comprising:
   detecting, by a first attitude detection sensor provided in a first endoscope, a first attitude of a first insertion section of the first endoscope;
   detecting, by a first insertion length detection sensor, a first insertion length of the first insertion section of the first endoscope when the first insertion section is inserted from a hole provided in a casing in which the rotor is housed;
   making a comparison between the first attitude detected by the first attitude detection sensor and a second attitude of a second insertion section detected by a second attitude detection sensor provided in a second endoscope and capable of detecting a same attitude as the first attitude detected by the first attitude detection sensor at a time of acquisition of a still image of one of the blades in a state where an insertion axis of the second insertion section at the time of acquisition of the still image by the second endoscope and an insertion axis of the first insertion section coincide with each other;
   making a comparison between the first insertion length detected by the first insertion length detection sensor and a second insertion length of the second insertion section detected by a second insertion length detection sensor provided in the second endoscope and capable of detecting a same insertion length as the first insertion length detected by the first insertion length detection sensor at the time of acquisition of a still image of the blade picked up by the second endoscope having the second insertion section;
   outputting first match information indicating a match between the first insertion length and the second insertion length based on a result of the comparison between the first insertion length and the second insertion length; and
   outputting second match information indicating a match between the first attitude and the second attitude based on a result of the comparison between the first attitude and the second attitude.

9. The blade inspection method according to claim 8, wherein the first match information and the second match information are information for changing an indication with a predetermined first mark and information for changing an indication with a predetermined second mark, respectively, displayed on a display.

10. The blade inspection method according to claim 8, wherein the comparison between the first and second attitudes is made before the comparison between the first and second insertion lengths.

11. The blade inspection method according to claim 8, wherein the first and second attitudes are determined by an angle of rotation about the insertion axis of the first insertion section and an angle of rotation about the insertion axis of the second insertion section, respectively.

12. The blade inspection method according to claim 8, wherein the first insertion length detection sensor is provided in the first endoscope, detects two first distances from the first insertion section to two objects in two directions perpendicular to the insertion axis of the first insertion section and opposite to each other, and detects the first insertion length based on the two first distances detected.

13. The blade inspection method according to claim 8, wherein the first insertion length detection sensor is provided in the first endoscope, detects the distance between a grasping section of the first endoscope and a fixing implement that supports and fixes the first endoscope, and detects the first insertion length based on the distance detected.

14. The blade inspection method according to claim 8, wherein the first insertion length is detected based on an output from an encoder provided on a fixing implement that supports and fixes the first endoscope.

15. The blade inspection method according to claim 12, wherein the two objects are stator vanes provided on a stator of the engine.

* * * * *